US005869634A

United States Patent [19]
Lambowitz et al.

[11] Patent Number: 5,869,634
[45] Date of Patent: Feb. 9, 1999

[54] METHOD OF MAKING AN RNA PARTICLE FOR USE IN CLEAVING NUCLEIC ACID MOLECULES AND INSERTING A NUCLEIC ACID MOLECULE INTO THE CLEAVAGE SITE

[75] Inventors: Alan M. Lambowitz; Steven Zimmerly; Jian Yang; Huatao Guo, all of Columbus, Ohio

[73] Assignee: The Ohio State Research Foundation, Columbus, Ohio

[21] Appl. No.: 946,617

[22] Filed: Oct. 7, 1997

Related U.S. Application Data

[62] Division of Ser. No. 526,964, Sep. 12, 1995, Pat. No. 5,698,421.

[51] Int. Cl.⁶ .......................... C07H 21/02; C07K 14/00; C12P 19/34; C12Q 1/68
[52] U.S. Cl. ..................... 536/23.1; 530/350; 435/91.31; 435/91.3; 435/91.51; 435/6; 435/91.32
[58] Field of Search ........................... 435/6, 91.2, 91.31, 435/91.3, 91.51, 91.53, 22.1, 91.32; 536/24.5, 23.1; 935/77; 530/350

[56] References Cited

U.S. PATENT DOCUMENTS

| 5,180,818 | 1/1993 | Cech et al. ............................ 536/23.1 |
| 5,498,531 | 3/1996 | Jarrell ................................... 435/91.31 |

OTHER PUBLICATIONS

"Group I and Group II introns" by Saldanha, et al., *The FASEB Journal,* vol. 7, Jan. 1993, pp. 15–24.
"Group II Intron Mobility Occurs to Target DNA–Primed Reverse Transcription" by Zimmerly, et al. *Cell,* vol. 82, Aug. 25, 1995, pp. 545–554.
"An Expanding Universe of Introns" by Belfort *Science,* vol. 262, Nov. 12, 1993, pp. 1009–1010.
"Integration of Group II Intro bII into a Foreign RNA by Reversal of the Self–Splicing Reaction in Vitro", by Mörl and Schmeizer *Cell,* vol. 60, Feb. 23, 1990, pp. 629–636.

"A Group II Intron RNA is a Catalytic Component of a DNA Endonuclease Involved in Intron Mobility" by Zimmerly, et al., *Cell,* vol. 83, Nov. 17, 1995, pp. 1–10.
"RNA enzymes (ribozymes) as antiviral therapeutic agents" by Rossi and Sarver *Tibtech* vol. 8, Jul. 1990, pp. 179–183.
"Mobile Group II Introns of yeast Mitochondrial DNA are Novel Site–Specific Retroelements" by Moran, et al., *Molecular and Cellular Biology,* vol. 15, No. 5, May 1995, pp. 2828–2838.
"Evolutionary relationships among group II intron–encoded proteins and identification of a conserved domain that may be related to maturase function" by Mohr, et al., *Nucleic Acids Research* vol. 21, No. 22, 1993, pp. 4991–4997.
"Reverse Transcriptase Activity Associated with Manturase–Encoding Group II Introns in Yeast Mitochndria", by Kennel, et al., *Cell,* vol. 73, Apr. 9, 1993, pp. 133–146.
"Introns as Mobile Genetic Elements" by Lambowitz, et al., *Annual Reviews Biochem,* vol. 62, pp. 587–622, 1993.

*Primary Examiner*—W. Gary Jones
*Assistant Examiner*—Debra Shoemaker
*Attorney, Agent, or Firm*—Calfee, Halter & Griswold LLP

[57] ABSTRACT

The present invention provides new methods, employing a nucleotide integrase, for cleaving double-stranded and single stranded DNA substrates at specific sites and for attaching nucleic acid molecules to the cleaved DNA substrates. One method uses a nucleotide integrase to cleave one strand of a double-stranded DNA and to concomitantly attach a nucleic acid molecule to the cleaved strand. Another method uses a nucleotide integrase to cleave both strands of a double-stranded DNA substrate and to attach a nucleic acid molecule to one strand of the DNA substrate. Another method uses a nucleotide integrase to cleave both strands of a double-stranded DNA substrate and to attach an RNA molecule to one strand of the substrate and for attaching a cDNA to the other strand of the substrate. Another method cleaves single stranded DNA with the concomitant insertion of a nucleic acid molecule at the cleavage point. The nucleotide integrase comprises an RNP particle which comprises a group II intron RNA bound to a group II intron encoded protein. The present invention also relates to purified and reconstituted RNP particles and reconstituted RNP that cleave DNA substrates.

3 Claims, 3 Drawing Sheets

METHOD OF MAKING AN RNA PARTICLE
FOR USE IN CLEAVING NUCLEIC ACID
MOLECULES AND INSERTING A NUCLEIC
ACID MOLECULE INTO THE CLEAVAGE
SITE

This is a divisional of application Ser. No. 08/526,964 filed on Sep. 12, 1995, now U.S. Pat. No. 5,698,421.

The present invention was made with support from National Institutes of Health Grant NO. GM37949. The United States Government has certain rights in the invention.

BACKGROUND

In recent years, a number of methods and biomolecules have been developed for manipulating DNA. Some of these biomolecules are used to cut or cleave DNA, which in some instances renders the substrate DNA nonfunctional. Other biomolecules are used to facilitate insertion of new pieces of nucleic acid into the cleavage site of the DNA substrate. The insertion of new segments of nucleic acid into the cleavage sites of the DNA substrate changes the characteristics of the RNA or protein molecules encoded by the substrate DNA molecules. Accordingly, the biomolecules which catalyze the cleavage of DNA substrates or the insertion of new nucleic acid molecules into the DNA substrates are useful tools for genetic engineering, for analytical studies and for diagnostic studies. One such molecule used for cleaving DNA substrates is the restriction endonuclease.

Restriction endonucleases are enzymatic proteins that cleave double-stranded DNA. Such endonucleases recognize specific nucleotide sequences in double-stranded DNA, and cleave both strands within or near the specific recognition site. Such specificity renders the restriction endonucleases important tools in the controlled fragmentation of double-stranded DNA. Restriction endonucleases are also useful analytical tools for determining whether certain sequences are present in substrate DNA and in genomic sequencing studies.

However, restriction endonucleases only cleave DNA substrates; they do not insert new nucleic acid molecules into the cleaved DNA substrate. Accordingly, another biomolecule is needed to insert new pieces of DNA or RNA into the double-stranded DNA.

Ribozymes are catalytic RNA molecules that cleave RNA and, in certain circumstances, that insert new pieces of RNA into the cleavage site of the RNA substrate. Unfortunately, ribozymes have not been particularly useful for cleaving DNA. Ribozymes cut only single-stranded DNA and only under extreme conditions of elevated temperatures and high concentrations of magnesium. The ribozymes have not been found to cleave double-stranded DNA. Ribozymes can be used to cleave double-stranded DNA only after the DNA is denatured and separated into two pieces of single stranded DNA.

Accordingly, it would be desirable to have a tool that cleaves double stranded DNA at specific sites and simultaneously inserts a new nucleic acid molecule into the cleavage site of the double-stranded DNA.

SUMMARY OF THE INVENTION

The present invention provides new methods, employing a nucleotide integrase, for cleaving double stranded and single stranded DNA substrates at specific sites and for inserting nucleic acid molecules into the cleaved DNA substrate. Thus, the nucleotide integrase is a useful tool, particularly for genome mapping and for genetic engineering.

One method uses a nucleotide integrase to cleave one strand of double-stranded DNA at a specific site and to concomitantly attach a nucleic acid molecule, which comprises an RNA molecule, to the cleaved strand at the cleavage site. Another method uses a nucleotide integrase for cleaving both strands of double-stranded DNA and for attaching a nucleic acid molecule, which comprises an RNA molecule, to one strand of the DNA substrate. Preferably, the nucleic acid molecule is fully integrated into the cleavage site. Another method uses a nucleotide integrase for cleaving both strands of double-stranded DNA and for attaching an RNA molecule to one strand of the DNA substrate at the cleavage site and for attaching a cDNA to the other strand of the DNA substrate at the cleavage site. Preferably, the RNA molecule is fully integrated into the cleavage site of the one strand. Another method provides for cleavage of single stranded DNA with the concomitant insertion of a nucleic acid at the cleavage point.

The nucleotide integrase comprises a group II intron RNA and a group II intron encoded protein, which is bound to the group II intron RNA. The nucleotide integrase includes at least two forms: a ribonucleoprotein particle, also referred to herein as "RNP particle"; and a reconstituted particle.

The RNP particle comprises an excised group II intron RNA and a group II intron-encoded protein, bound to the excised group II intron RNA. The excised group II intron RNA of the RNP particle has a hybridizing region which is complementary to a recognition site on the substrate DNA. Preferably, the group II intron RNA has six domains. The group II intron-encoded protein of the RNP particle preferably has an X domain and a Zn domain. The X domain of the protein has a maturase activity. The Zn domain of the protein has $Zn^{2+}$ finger-like motifs.

The reconstituted particle is a synthetic particle that is purified from a reconstituted RNP particle preparation. The reconstituted RNP particle preparation is made by combining a group II intron RNA-protein complex, also referred to as the "RNA-protein complex" and an exogenous nucleic acid, preferably an excised group II intron RNA, hereinafter also referred to as "exogenous RNA". The RNA-protein complex contains a group II intron-encoded protein that is associated with RNA that is free of the excised group II intron RNA having a sequence which encodes the group II encoded protein. The intron-encoded protein has an X domain and a Zn domain. The exogenous RNA has a hybridizing region which is complementary to a recognition site on the substrate DNA. Preferably, the exogenous RNA has six domains.

The present invention also relates to certain embodiments of the nucleotide integrase.

DETAILED DESCRIPTION OF THE INVENTION

The present invention provides new methods that employ a nucleotide integrase for manipulating a DNA substrate.

The methods enable double-stranded DNA substrates to be cleaved at specific sites and nucleic acid molecules to be inserted into the cleaved DNA substrate. One method uses a nucleotide integrase to cleave one strand of double-stranded DNA at a specific site and to concomitantly attach a nucleic acid molecule, which comprises an RNA molecule, to the cleaved strand at the cleavage point. Another method uses a nucleotide integrase for cleaving both strands of double-stranded DNA and for attaching a nucleic acid molecule, preferably an RNA molecule, to one strand of the DNA substrate at the cleavage point. Another method uses a nucleotide integrase to cleave both strands of double-stranded DNA and to attach a nucleic acid molecule, preferably an RNA molecule, to one strand of the DNA substrate and then to attach a cDNA molecule to the other strand of the DNA substrate at the cleavage site.

The nucleotide integrase

Figure 1:
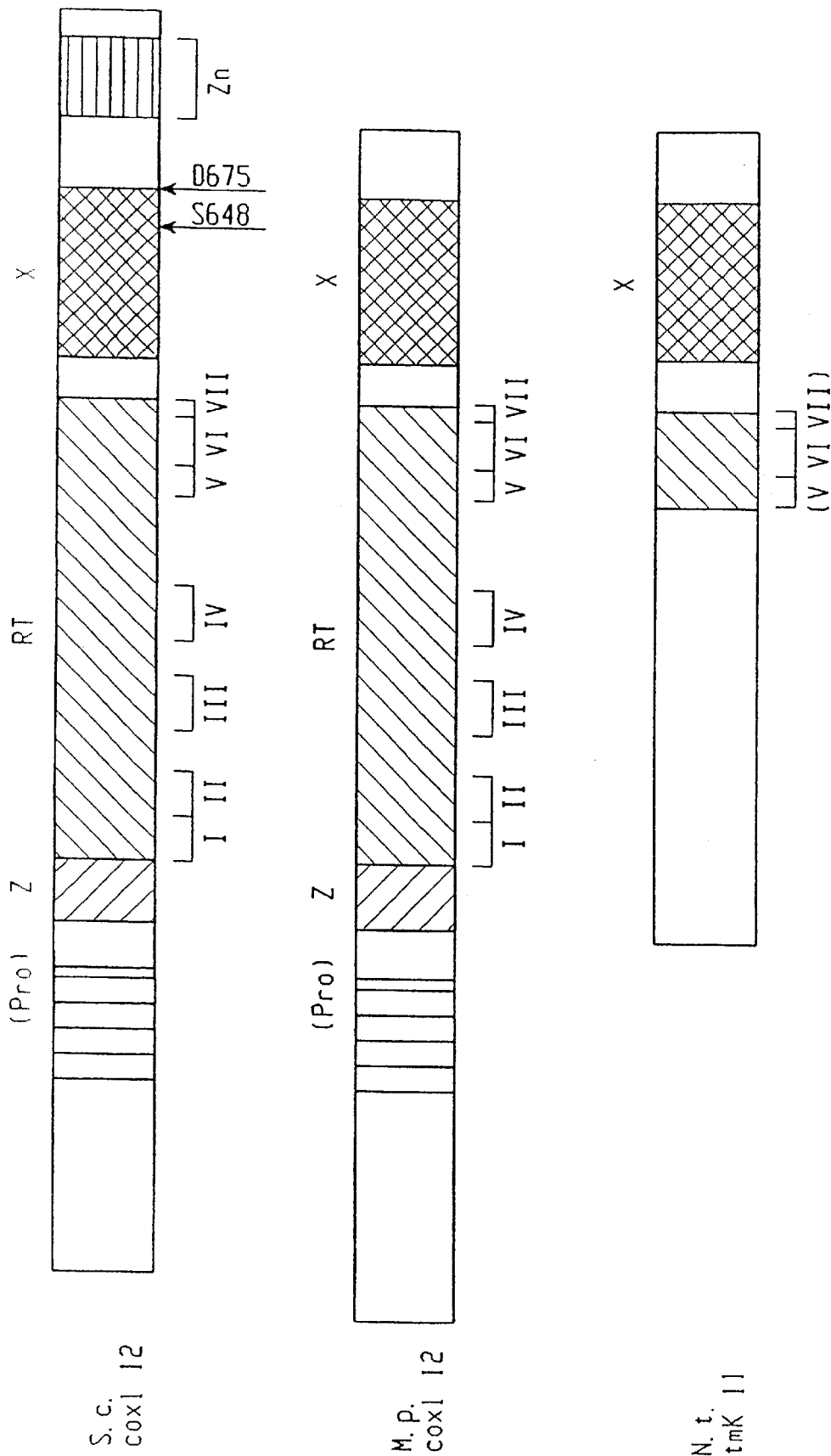
FIG. 1 is a diagram of the domains of the proteins which are encoded by the open reading frames of the group II intron 2 of the *S. cerevisiae* mitochondrial COX1 gene, the group II intron 2 of the *M. polymorpha* mitochondrial COX1 gene, and the group II intron 1 of the *N. tabacum* chloroplast trnK gene.

The nucleotide integrase comprises a group II intron encoded RNA and a group II intron encoded protein which protein is bound to the RNA. The group II introns comprise a specific type of intron which is present in the DNA of bacteria and in the DNA of organelles, particularly the mitochondria of fungi, yeast and plants and the chloroplast of plants. The group II intron RNA molecules, that is, the RNA molecules which are encoded by the group II introns, share a similar secondary and tertiary structure. The group II intron RNA molecules typically have six domains. Domain IV of the group II intron RNA contains the nucleotide sequence which encodes the "group II intron encoded protein." "Excised group II intron RNA," as used herein, refers to the RNA that is either an in vitro or in vivo transcript of the DNA of the group II intron and that lacks flanking exon sequences. "Group II intron encoded protein" as used herein, is a protein encoded by a group II intron. The domains of three representative group II intron-encoded proteins are depicted in FIG. 1.

The nucleotide integrase includes RNP particles isolated from wild type or mutant organisms and reconstituted RNP particles synthesized from exogenous RNA and a particle preparation which lacks the exogenous RNA.

The RNP particle

The RNP particle is used in an RNP particle preparation which, while isolated from organelles, still contains substantial amounts of ribosomes; or the RNP particle is used as a purified RNP particle which is substantially free of ribosomes.

The RNP particle and RNP particle preparation cleave both strands of the double-stranded DNA, catalyze the attachment of the excised, group II intron RNA molecule to one of the strands of the substrate DNA and catalyze the formation of a cDNA molecule on the other strand of the cleaved double-stranded DNA substrate.

The RNP particle comprises an excised group II intron RNA and a group II intron-encoded protein, which is bound to the excised group II intron RNA. The excised group II intron RNA of the RNP particle has at least one hybridizing region, which will hybridize a complementary recognition site on the substrate DNA. The hybridizing region has a nucleotide sequence, referred to hereinafter as the EBS sequence, which is complementary to the sequence, referred to hereinafter as the IBS sequence, of the recognition site of the intended substrate DNA. The group II intron-encoded protein of the RNP particle preferably has an X domain and a Zn domain. More preferably, the group II intron-encoded protein further comprises a reverse transcriptase domain.

The excised group II intron RNA is obtained from wild type organisms, or mutated organisms, by in vitro transcription, or by in vitro transcription and splicing from the transcript of a modified or unmodified group II intron. Nucleotide integrases in which the group II intron RNA has nucleotide base changes in the hybridizing region, as compared to the wild type, typically have altered specificity for the substrate DNA of the nucleotide integrase. The group II intron RNA also includes modified group II intron RNA molecules that have nucleotide base changes or additional nucleotides in the internal loop regions of the group II intron RNA, preferably the internal loop region of domain IV.

The group II intron-encoded protein preferably has an X domain and a Zn domain. The group II intron-encoded protein includes proteins isolated from wild type organisms or from mutant organisms. In addition to the conventional group II intron encoded proteins, other proteins suitable as components of the nucleotide integrase include modified group II intron encoded proteins which have additional amino acids at the N terminus, or C terminus, or alterations in the internal regions of the protein. Preferably, the group II-intron encoded protein has a reverse transcriptase domain.

The Reconstituted particle

The reconstituted particle is used in a reconstituted RNP particle preparation which, while isolated from organelles, still contains substantial amounts of ribosomes; or the reconstituted particle is used as a purified reconstituted RNP particle which is substantially free of ribosomes.

The reconstituted particle is useful for cleaving one strand of a double-stranded DNA substrate and attaching an RNA molecule to the cleaved strand at the cleavage point; cleaving both strands of the double-stranded DNA substrate and catalyzing the insertion of an RNA molecule into the cleavage site of one strand of the DNA substrate; cleaving both strands of a double-stranded DNA substrate and attaching a nucleic acid molecule to both strands at the cleavage points.

The reconstituted RNP particle preparation comprises an exogenous excised group II intron RNA, an RNA-protein complex, and a reconstituted RNP particle which comprises the exogenous group II intron RNA bound to a group II intron-encoded protein.

The RNA-protein complex contains a group II intron-encoded protein that is associated with RNA that is free of the excised, group II RNA molecules having a sequence which encodes the group II intron-encoded protein. The group II intron-encoded protein comprises an X domain and a Zn domain and includes both unmodified and modified group II intron-encoded proteins. The X domain of the protein has a maturase activity. The Zn domain of the protein has $Zn^{2+}$ finger-like motifs. More preferably, the group II intron-encoded protein further comprises a reverse transcriptase domain. The group II intron-encoded protein has a binding affinity for the RNA of the complex and for the exogenous excised group II intron RNA.

The exogenous group II intron RNA of the RNP particle has at least one hybridizing region which is complementary to a recognition site on the substrate DNA. The exogenous RNA preferably has six domains. The exogenous RNA includes both unmodified and modified group II intron RNA molecules. Preferably, the exogenous RNA is an in vitro transcript or a derivative of an in vitro transcript of an unmodified or modified intron group II intron. For example, the exogenous RNA may be derived by splicing from an in vitro transcript. In a preferred embodiment of the reconstituted particle, the exogenous RNA has the sequence encoded by the DNA sequence of SEQ.ID.NO.1 and the group II intron-encoded protein is a 62 kDa protein that is processed from a polypeptide having the sequence of SEQ.ID.NO.4.

Methods for Cleaving DNA and Inserting Nucleotides

The methods of the present invention and the reconstituted RNP particles are useful analytical tools for determining the location of a defined sequence in a double-stranded DNA substrate. Moreover, the simultaneous insertion of the nucleic acid molecule into the first strand of DNA permits tagging of the cleavage site of the first strand with a radiolabeled molecule. In addition, the automatic attachment of an RNA molecule onto one strand of the DNA substrate permits identification of the cleavage site through hybridization studies that use a probe that is complementary to the attached RNA molecule. An attached RNA molecule that is tagged with a molecule such as biotin also enables the cleaved strand to be affinity purified. These methods are also useful for rendering the substrate DNA nonfunctional or for changing the characteristics of the RNA and protein encoded by the substrate DNA.

While a wide range of temperatures are suitable for the methods herein, good results are obtained at a reaction temperature of from about 30° C. to about 42° C., preferably from about 30° to about 37° C. A suitable reaction medium contains a monovalent cation such as $Na^+$ or $K^+$, at a concentration from about 0 to about 300 mM; preferably from about 50 to about 200 mM KCl, and a divalent cation, preferably a magnesium or manganese ion, more preferably a magnesium ion, at a concentration that is less than 100 mM and greater than 1 mM. Preferably the divalent cation is at a concentration of about 5 to about 20 mM, more preferably about 10 to about 20 mM. The rate of attachment of the intron RNA to the cleaved sense strand at 5 mM $MgCl_2$ is about 25% of the rate that is obtained using 10–20 mM $MgCl_2$. The preferred pH for the medium is from about 6.0–8.5, more preferably about 7.5–8.0.

Cleaving one strand of double stranded DNA

Double stranded DNA substrate having a recognition site is cleaved and RNA inserted at the cleavage site by reacting the substrate DNA with a nucleotide integrase. Suitable nucleotide integrases include: a mitochondrial RNP particle from mutant yeast strain $1o2^{HHVR}$ which comprises a modified, excised RNA from the group II intron aI2 of the yeast mitochondrial COX1 gene and an aI2-encoded protein that has a missense mutation in the HHVR motif; a mitochondrial RNP particle from mutant yeast strain $1^o2^{ConZn}$ which comprises a modified, excised aI2 intron RNA and an aI2-encoded protein that lacks the most conserved motifs in the Zn domain; a mitochondrial RNP particle from mutant yeast strain $1^o2^{C-C/2}$ that comprises a modified, excised aI2 intron RNA and an aI2-encoded protein that has a missense mutation in the second $Zn^{+2}$ finger-like motif.

The most preferred reaction conditions for attachment of the intron RNA to the cleaved strand of substrate DNA are 100 mM KCl, 20 mM $MgCl_2$, pH 7.5, 5 mM DTT and 37° C.

Cleaving both strands of double stranded DNA

Both strands of a DNA substrate having a recognition site are cleaved by reacting nucleotide integrases with the DNA. Suitable nucleotide integrases include, for example: a mitochondrial RNP particle that comprises an excised aI2 RNA and aI2-encoded protein, a mitochondrial RNP particle that comprises aI1 RNA and aI1 intron-encoded protein; a mitochondrial RNP particle from mutant yeast strain $1^o2^{YAHH}$ which comprises a modified, excised aI2 RNA and an aI2-encoded protein that has the mutation YADD→YAHH in the reverse transcriptase domain of the protein; and a reconstituted RNP particle which comprises an exogenous excised aI2 RNA and an aI2-encoded protein. The most preferred reaction conditions for cleavage of both strands of the DNA substrate by the nucleotide integrase, are 100 mM KCl, 20 mM $MgCl_2$, pH 7.5, 5 mM DTT and 37° C.

Under these conditions, the nucleotide integrase which comprises an excised aI1 RNA and an aI1 encoded protein cleaves and inserts the aI1 RNA into the cleavage site of the sense strand of a double-stranded DNA substrate which contains the target sequence of SEQ. ID. NO. 17, in the sense strand. In this sequence, nucleotide bases 63–69 having the sequence 5'TTAATG, hereinafter designated as "IBS1," are complementary to nucleotide bases, hereinafter referred to as "EBS1," in domain I of the aI1 intron RNA. Nucleotide bases 57–62 which have the sequence 5'CAGTTA, hereinafter designated as "IBS 2," are complementary to other nucleotide bases, hereinafter referred to as "EBS2," in domain I of the aII intron RNA. The RNP particles of this nucleotide integrase cleave the sense strand of this substrate between nucleotide 69 and nucleotide 70 of the target sequence, and cleave the antisense strand of this substrate 10 base pairs downstream from cleavage site of the sense strand.

Under these conditions, a nucleotide integrase which comprises an excised aI2 RNA and an aI2 encoded protein cleaves and inserts the aI2 RNA into the cleavage site of the sense strand of a double-stranded DNA substrate which contains the target sequence 5'TTTTAGTAGCTGGTCATGCTGTATTAATAATTTTCTTCTTAG-TAATGCCTGCTTTAATAG GAGGTTTTGGT), SEQ. ID. NO. 5, in the sense strand. In this sequence, nucleotide bases 31–36 having the sequence 5'TTTTCT, hereinafter designated as "IBS3," are complementary to nucleotide bases, hereinafter referred to as "EBS3, " in domain I of the aI2 intron RNA. Nucleotide bases 24–30, which have the sequence 5'TTAATAA, hereinafter designated as "IBS4," are complementary to other nucleotide bases, hereinafter referred to as "EBS4," in domain I of the aI2 intron RNA. The RNP particles of this nucleotide integrase cleave the sense strand of this substrate between nucleotide 36 and nucleotide 37 of the target sequence, and cleave the antisense strand of this substrate 10 base pairs downstream from cleavage site of the sense strand.

Cleaving DNA, insertion of RNA and formation of cDNA

Both strands of a DNA substrate having a recognition site are cleaved and an RNA attached to one strand of the DNA and a cDNA attached to the cleaved second strand of the DNA substrate by incubating the DNA with the nucleotide integrase in the presence of deoxynucleotides. Suitable nucleotide integrases include, for example: a mitochondrial RNP particle that comprises an excised aI2 RNA and aI2-encoded protein and a mitochondrial RNP particle that comprises aI1 RNA and aI1 intron-encoded protein.

Suitable conditions for the nucleotide integrase-catalyzed synthesis of a cDNA on the second strand of the DNA substrate include a reaction temperature of from about 30° to about 45° C., preferably from about 37° to about 42° C. The preferred reaction medium includes a monovalent cation such as $Na^+$ or $K^+$, at a range of 0–300 mM, preferably from about 50 mM to about 150 mM KCl, and a divalent cation, preferably a magnesium or manganese ion, more preferably a magnesium ion at a concentration range of from about 2 mM to about 20 mM. The preferred pH for the medium is about 7.5 to about 8.5. The most preferred conditions for synthesis of an elongated cDNA product are 100 mM KCl, 2 mM $MgCl_2$, 5 mM DTT, pH 8.5, and 37° C. The most preferred conditions for maximum cleavage of the second strand and the formation of a cDNA product is 100 mM KCl, a $Mg^{2+}$ concentration of 10 to 20 mM, 5 mM DTT and a pH of 7.5.

Cleavage of single stranded DNA

Single stranded DNA substrate having a recognition site is cleaved and RNA inserted at the cleavage site by reacting the substrate DNA with a nucleotide integrase. Suitable nucleotide integrases include for example: a mitochondrial RNP particle that comprises an excised aI2 RNA and aI2-encoded protein and a mitochondrial RNP particle that comprises aI1 RNA and aI1 intron-encoded protein.

The most preferred reaction conditions for cleavage of the substrate and insertion of the intron RNA into the cleavage site by the nucleotide integrase, are 100 mM KCl, 20 mM $MgCl_2$, pH 7.5, 5 mM DTT and 37° C. Under these condition, the nucleotide integrase which comprises an aI2 intron RNA and an aI2 encoded protein cleaves and inserts an aI2 RNA into the cleavage site of a single-stranded DNA substrate that contains the IBS3 sequence 5'TTTTCT or the IBS4 sequence 5'TTAATAA. In contrast, the aI2 RNA alone is unable to cleave double stranded DNA or single stranded DNA at the 20 mM $Mg^{2+}$ concentration typically used in the methods of the present invention.

Preparation of the Nucleotide Integrase

The nucleotide integrase is isolated from wild type or mutant yeast mitochondria, fungal mitochondria, plant mitochondria, chloroplasts, the proteotobacterium *Azotobacter vinelandii*, the cyanobacterium Calothrix, and *Escherichia coli*. The procedure for isolating the RNP particle preparation involves mechanically and/or enzymatically disrupting the cell membranes and or cell walls of the organisms. In the case of fungi and plants, the purification also involves separating the specific organelles, such as mitochondria or chloroplasts, from the other cellular components by differential centrifugation and/or flotation gradients and then lysing the organelles with a nonionic detergent, such as Nonidet P-40. The organelle and bacterium lysates are then centrifuged through a sucrose cushion to obtain the ribonucleoprotein (RNP) particle preparation. The RNP particles may be further purified by separation on a sucrose gradient, or a gel filtration column, or by other types of chromatography.

The reconstituted RNP particle preparation is prepared by combining an RNA-protein complex preparation with an exogenous excised group II intron RNA. The RNA-protein complex is preferably isolated from a yeast, fungi, or bacterium using the protocol for RNP particles described above. The RNA-protein complex comprises a group II intron-encoded protein and RNA that is free of the excised group II intron RNA having a sequence that encodes the group II intron-encoded protein.

The exogenous RNA preferably is made by in vitro transcription or by in vitro transcription and self-splicing of the group II intron. The exogenous RNA may also be made by isolation of the group II intron RNA from cells or organelles in which it is naturally present or from cells in which an altered intron has been inserted and expressed. The exogenous RNA is then added to a preparation containing the RNA-protein complex. Preferably, the exogenous group II intron RNA is first denatured. The exogenous RNA is added to the RNA-protein complex on ice.

EXAMPLES

The RNP particle preparations of the following examples 1–10, the RNA-protein complex of the example 12, and the preparations of comparative examples A–D were isolated from the mitochondria of the wild-type *Saccharomyces cerevisiae* yeast strain ID41-6/161 MATa ade1 lys1, hereinafter designated "161", and derivatives thereof. The mitochondria of the wild-type yeast strain 161 contains a COX1 gene that includes the group II intron aI1 and the group II intron aI2.

The COX1 gene in the mutant yeast strains either lacks one of the group II introns or has a mutation in one of the group II introns. The excised group II intron RNA molecules and the group II intron encoded proteins are derived from the group II introns aI1 and aI2 that are present in the wild-type and mutant yeast strains.

Figure 2:
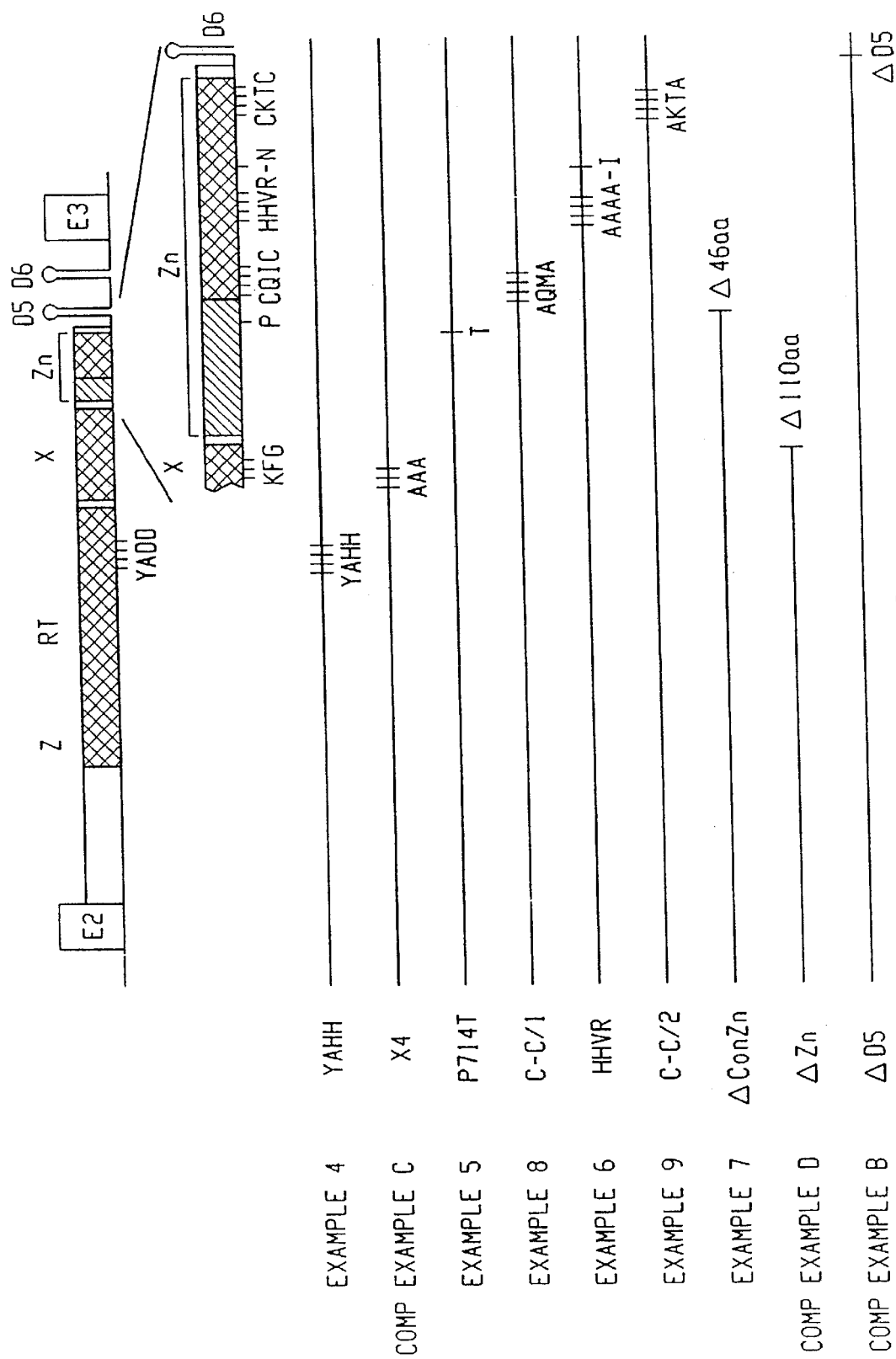
FIG. 2 is a chart which depicts the locations of the mutations in the group II intron encoded proteins that are present in the nucleotide integrases of examples 4–9 and the RNP particles of comparative examples B–D.

FIG. 2 depicts several of the mutations/modifications that are present in the aI2-encoded proteins that are produced by the different mutant yeast strains. The intron composition of the COX1 gene in the different yeast strains is denoted by a convention in which a superscript "+" indicates the presence of the aI1 intron or the aI2 intron, a superscript "o" indicates the absence of the aI1 or aI2 intron, and other superscripts refer to specific alleles or mutations in the aI2 intron.

Example 1

An RNP particle preparation was isolated from the mitochondria of the Saccharomyces cerevisiae wild-type yeast strain 161. The intron composition of the COX1 gene of the wild-type strain is $1^{+'}2^{+'}$. The RNP particle preparation contains an RNP particle that is derived from the aI1 intron and includes an excised, aI1 RNA bound to a protein encoded by aI1. The preparation also contains an RNP particle that is derived from the aI2 intron and that comprises a excised aI2 RNA molecule and an associated aI2-encoded protein.

To prepare the RNP particle preparation, the yeast were inoculated into a 1 liter liquid culture medium containing 2% raffinose, 2% BactoPeptone from Difco and 1% yeast extract from Difco to an $O.D._{595}$ of 1.6–1.7. The cell walls were digested with 40 mg of the yeast lytic enzyme from ICN, and the cells broken by mechanical disruption with glass beads. The nuclei and cell debris were pelleted from the lysate by centrifugation for 5 minutes in a Beckman GSA rotor at 5,000 rpm. The supernatant was removed and centrifuged in a Beckman GSA rotor at 13,000 rpm for 15 minutes to obtain a mitochondrial pellet. The mitochondria were layered on a flotation gradient consisting of a 44% sucrose solution layer, a 53% sucrose solution layer, and a 65% sucrose solution layer and centrifuged in a Beckman SW28 rotor at 27,000 rpm for 2 hours and 10 minutes. The mitochondria were collected from the 53%/44% interface and suspended in buffer containing 0.5M KCl, 50 mM $CaCl_{2,}$ 25 mM Tris-HCl, pH 7.5, 5 mM DTT and lysed by the addition of Nonidet P-40 to a final concentration of 1%. The mitochondrial lysate was then centrifuged in a Beckman 50Ti rotor at 50,000 rpm for 17 hours through a 1.85M sucrose cushion in a buffer containing 0.5M KCl, 25 mM $CaCl_{2,}$ 25 mM Tris-HCl, pH 7.5, 5 mM DTT, to obtain a pellet of RNP particles that were largely free of mitochondrial proteins. The isolated RNP particles were resuspended in 10 mM Tris-HCl, pH 8.0 and 1 mM DTT and stored at −70° C. The preparation may be repeatedly thawed and frozen before use.

Example 1a

Purified RNP particle 2.5 $O.D._{260}$ of the RNP particles from example 1 in a volume of 150 µl were layered onto a 12 ml 5–20% linear sucrose gradient in a buffer consisting of 100 mM KCl, 2 mM $MgCl_{2,}$ 50 mM Tris-HCl, pH 7.5, and 5 mM DTT. The gradient was centrifuged in an SW41 rotor at 4° C. at 40,000 rpm for five hours. The gradient was fractionated into 35 fractions of approximately 325 µl. Fractions 12–20 contain the purified RNP particles which are substantially free of ribosomal RNA. The location of the RNP particles in the gradient fractions was independently verified by Northern hybridization with aI2 antisense RNA. The location of the small and large subunits of ribosomal RNA in the gradient fractions was independently verified by ethidium bromide staining of the fractions on a 1% agarose gel.

Example 2

RNP particle preparation from mutant yeast strain $1°2^+$

The RNP particles comprise an excised aI2 RNA and an aI2-encoded protein. Yeast strain $1°2^{+t}$ was obtained from Dr. Philip S. Perlman at the University of Texas Southwestern Medical Center and was prepared as described in Moran et al., 1995, Mobile Group II Introns of Yeast Mitochondrial DNA Are Novel Site-Specific Retroelements, Mol. Cell Biol. 15, 2838–38, which is incorporated herein by reference. The $1°2^{+t}$ mutant strain was constructed as follows: (i) the aI2 intron from strain 161 was cloned as a ClaI-to-BamHI fragment into pBluescript KS$^+$ obtained from Stratagene to yield pJVM4; (ii) pJVM4 was cleaved with ClaI and NdeI to remove the 5' end of the insert; and (iii) an MspI-to-NdeI fragment that contains exons 1 and 2 of the mitochondria COX1 gene plus the 5' end of aI2 from yeast strain C1036ΔI was inserted to yield plasmid pJVM164. Yeast strain C1036ΔI, in which aI1 is excised from the mitochondrial DNA, was prepared as described in Kennell et al., 1993, Reverse transcriptase activity associated with maturase-encoding group II introns in yeast mitochondria. Cell 73, 133–146, which is incorporated herein by reference. pJVM164 was transformed into a [rho$^0$] strain, and the $1°2^{+t}$ allele was placed into an intact mitochondrial DNA by recombination. This last step is accomplished by mating to a nonreverting COX 1 mutant derived from mutant C1036 (strain 5B), whose construction is described in Kennel et al., 1993, and selecting for recombinant progeny that are capable of respiring and growing on glycerol-containing medium (GLY$^+$) and that contain the transformed COX 1 allele in place of the 5B allele.

The reactions and manipulations directed at cloning DNA, such as ligations, restriction enzyme digestions, bacterial transformation, DNA sequencing etc. were carried out according to standard techniques, such as those described by Sambrook et al., *Molecular cloning: a laboratory manual*, 2nd ed., Cold Spring Harbor Laboratory Press. Cold Spring Harbor. N.Y. Yeast mitochondrial transformations were also carried out according to standard techniques such as those described in Belcher et al., 1994, Biolistic transformation of mitochondria in *Saccharomyces cerevisiae*, 101–115. In N.-S. Yang and P. Christou (ed.) *Particle Bombardment Technology for Gene Transfer*. Oxford University Press, New York. The RNP particle preparation was made from the mitochondria of mutant yeast strain $1°2^+$, as in Example 1.

Example 3

RNP particle preparation from mutant yeast strain $1^{+t}2°$

Yeast strain $1^{+t}2°$ is a derivative of the wild-type yeast strain 161. The yeast strain $1^{+t}2°$ was obtained from Dr. Philip S. Perlman and was prepared as described in Kennell et al., 1993. Cell 73, 133–146. Yeast strain $1^{+t}2°$ contains a segment of the COX 1 gene of *S. diastaticus*, which lacks aI2, inserted into wild-type 161 mtDNA via mitochondrial transformation. The construction started with plasmid pSH2, which contains aI1 from wild-type 161 and some flanking sequences cloned as a HpaII/EcoRI fragment in pBS$^+$ (Stratagene, La Jolla, Calif.). That plasmid was cleaved near the 3' end of aI1 with ClaI and in the downstream polylinker with BamHI, and the gap was filled with a ClaI/BamHI fragment from *S. diastaticus* mitochondrial DNA (NRRL Y-2416) that contains the 3' end of aI1, E2, E3 and most of aI3, thus creating a $1^{+t}2°$ form of the COX 1 gene. The plasmid containing the hybrid COX 1-$1^{+t}2°$ segment was transformed into ρ$^°$ derivative of strain MCC109 (MATα ade2-101 ura3-52 kar1-1) by biolistic transformation. The resulting artificial petite was crossed to strain n161/m5B, and gly$^+$ recombinants containing the COX 1 $1^{+t}2°$ allele in the n161 background were isolated. The hybrid aI1 allele, which is spliced normally, differs from that of wild-type 161 by one nucleotide change, C to T, at position 2401, changing Thr$_{744}$ to Leu in the intron open reading frame. The RNP particle preparation was made from the mitochondria of mutant yeast strain $1^+2°$ as in Example 1. The RNP particles comprise an excised aI1 RNA molecule and an aI1 encoded protein.

Example 4

RNP particle preparation from mutant yeast strain $1°2^{YAHH}$

Yeast strain $1°2^{YAHH}$ was obtained from Dr. Philip S. Perlman and was made as described in Moran et al., 1995, Mol. Cell Biol. 15, 2838–38., using a mutagenized pJVM164 plasmid. The allele was made by oligonucleotide-directed mutagenesis of pJVM164 which contains a 4.4 kb MspI/BamHI fragment extending from 217 nucleotides upstream of exon 1 through intron aI3 of the COX1 allele. The mutagenesis changes the aI2 nucleotides 1473 to 1478 from GAT GAT to CAT CAT (D-491D-492 to HH). The RNP particles comprise a mutated, excised aI2 RNA and an aI2-encoded protein that has the mutation YADD→YAHH in the reverse transcriptase domain of the protein. The RNP particle preparation was made from the mitochondria of mutant yeast strain $1°2^{YAHH}$ as in Example 1.

Example 5

RNP particles from the mutant yeast strain $1°2^{P714T}$

The mutant yeast strain $1°2^{P714T}$ was obtained from Dr. Philip S. Perlman and was constructed according to the procedure described in Kennell et al., 1993, *Cell* 73, 133–146, where it is named n161/m161-C1036Δ1. The RNP particles comprise a mutated, excised aI2 intron RNA molecule and an aI2-encoded protein that carries the missense mutation P$_{714}$T in the Zn domain. The RNP particle preparation was made from mitochondria of mutant yeast strain $1°2^{P714T}$ as in Example 1.

Example 6

RNP particle from mutant yeast strain $1°2^{HHVR}$

The mutant yeast strain $1°2^{HHVR}$ was obtained from Dr. Philip S. Perlman and was made as described in Moran et al., 1995, Mol. Cell Biol. 15, 2828–38, which is incorporated herein by reference, using a mutagenized pJVM164 plasmid. The allele was constructed by site-directed mutagenesis of pJVM164. The aI2 intron has the following changes: positions 2208–2219 of SEQ ID No:1 from CATCACGTAAGA to GCAGCTGCAGCT (H$_{736}$H$_{737}$V$_{738}$R$_{739}$ to AAAA) and A$_{2227}$A to T (N$_{742}$I). This nucleotide integrase preparation comprises a mutated, excised aI2 intron RNA and an aI2-encoded protein that has a missense mutation in the HHVR motif. The RNP particle preparation was made from mitochondria of mutant yeast strain $1°2^{HHVR}$.

Example 7

RNP particle from mutant yeast strain $1°2^{ConZn}$

The mutant yeast strain $1°2^{+ConZn}$ was obtained from Dr. Philip S. Perlman and was made as described in Moran et al., 1995, Mol. Cell Biol. 15, 2828–38, using a mutagenized pJVM164 plasmid. The allele was constructed by oligonucleotide-directed mutagenesis of pJVM164. The aI2 intron has the following changes: positions 2157–2165 changed from TTATTTAGT to TAATAATAA (L$_{719}$F$_{720}$S$_{721}$ to OchOchOch). RNP particles comprise a mutated, excised aI2 intron RNA and an aI2-encoded protein that lacks the most conserved motifs in the Zn domain. The RNP particle preparation was made from mitochondria of mutant yeast strain $1°2^{ConZn}$.

Example 8
RNP particle from mutant yeast strain $1°2^{C-C/1}$

The mutant yeast strain $1°2^{C-C/1}$ was obtained from Dr. Phillip S. Perlman and was made as described in Moran et al., 1995, using a mutagenized pJVM164 plasmid. The allele was constructed by site-directed mutagenesis of pJVM164. The aI2 intron has the following changes: positions 2172–2173 changed from TG to GC ($C_{724}A$) and 2180–2182 changed from TTG to AGC ($I_{726}C_{727}$ to MA). The RNP particles comprise a mutated, excised aI2 intron RNA and an aI2-encoded protein that has a missense mutation in the first $Zn^{+2}$-finger-like motif. The RNP particle preparation was made from mitochondria of mutant yeast strain $1°2^{C-C/1}$.

Example 9
RNP particles from mutant yeast strain $1°2^{C-C/2}$

The mutant yeast strain $1°2^{C-C/2}$ was obtained from Dr. Philip S. Perlman and was made as described in Moran et al., 1995, using a mutagenized pJVM164 plasmid. The allele was constructed by site-directed mutagenesis of pJVM164. The aI2 intron has the following changes: position 2304–2305 changed from TG to GC ($C_{768}A$) and 2313–2314 changed from TG to GC ($C_{771}A$). The RNP particles comprise a mutated excised aI2 intron RNA and an aI2-encoded protein that has a missense mutation in the second $Zn^{+2}$ finger-like motif. The RNP particle preparation was made from mitochondria of mutant yeast strain $1°2^{C-C/2}$.

Example 10
RNP particles from mutant yeast strain $1°2^{H6}$

The mutant yeast strain, obtained from Dr. Philip S. Perlman, was made by transferring the mutagenized plasmid pJVM164 into the mitochondria of yeast strain GRF18 as described in Moran et al., 1995. The allele was constructed by site directed mutagenesis of pJVM164 and has the sequence $(CAT)_6$ inserted between nucleotides 2357 and 2358 of the aI2 intron. The RNP particle preparation was made from mitochondria of mutant yeast strain $1°2^{H6}$ according to the protocol described above for example 1. The RNP particles comprise a mutated, excised aI2 intron RNA and an aI2-encoded protein that has six histidines added to the C terminus of the aI2-encoded protein.

Example 11
RNP particles from Neurospora intermedia.

Mitochondria from the Varkud strain of Neurospora intermedia, which is available from the Fungal Genetics Stock Center, were prepared as described in Lambowitz A.M. 1979, Preparation and analysis of mitochondrial ribosomes. Meth. Enzymol. 59, 421–433. The conidia were disrupted with glass beads and the mitochondria and RNP particles isolated as described in Example 1. The RNP particles comprise an excised coI intron RNA and the protein encoded by the coI intron.

Example 12
Reconstituted RNP particle preparation

A reconstituted RNP particle preparation was made by incubating an exogenous, excised, in vitro RNA transcript of the aI2 intron with an RNP preparation isolated from the mutant yeast strain $1°2^{\Delta D5}$, in which the aI2 intron RNA lacks a domain V and is therefore splicing defective. The mutant allele $1°2^{\Delta D5}$ was obtained from Dr. Philip S. Perlman and was constructed using the same procedure that was used to make yeast strain $1^+2^{\Delta D5}$ that was described in Moran et al. 1995, except that the final mating was with yeast strain $1°2^+$. The RNP preparation was isolated from $1°2^{\Delta D5}$ using the protocol described above in Example 1. The RNP preparation isolated from the mitochondria of $1°2^{\Delta D5}$ does not contain excised aI2 RNA but does contain aI2-encoded protein that is associated with other RNA molecules in the preparation.

Figure 3:
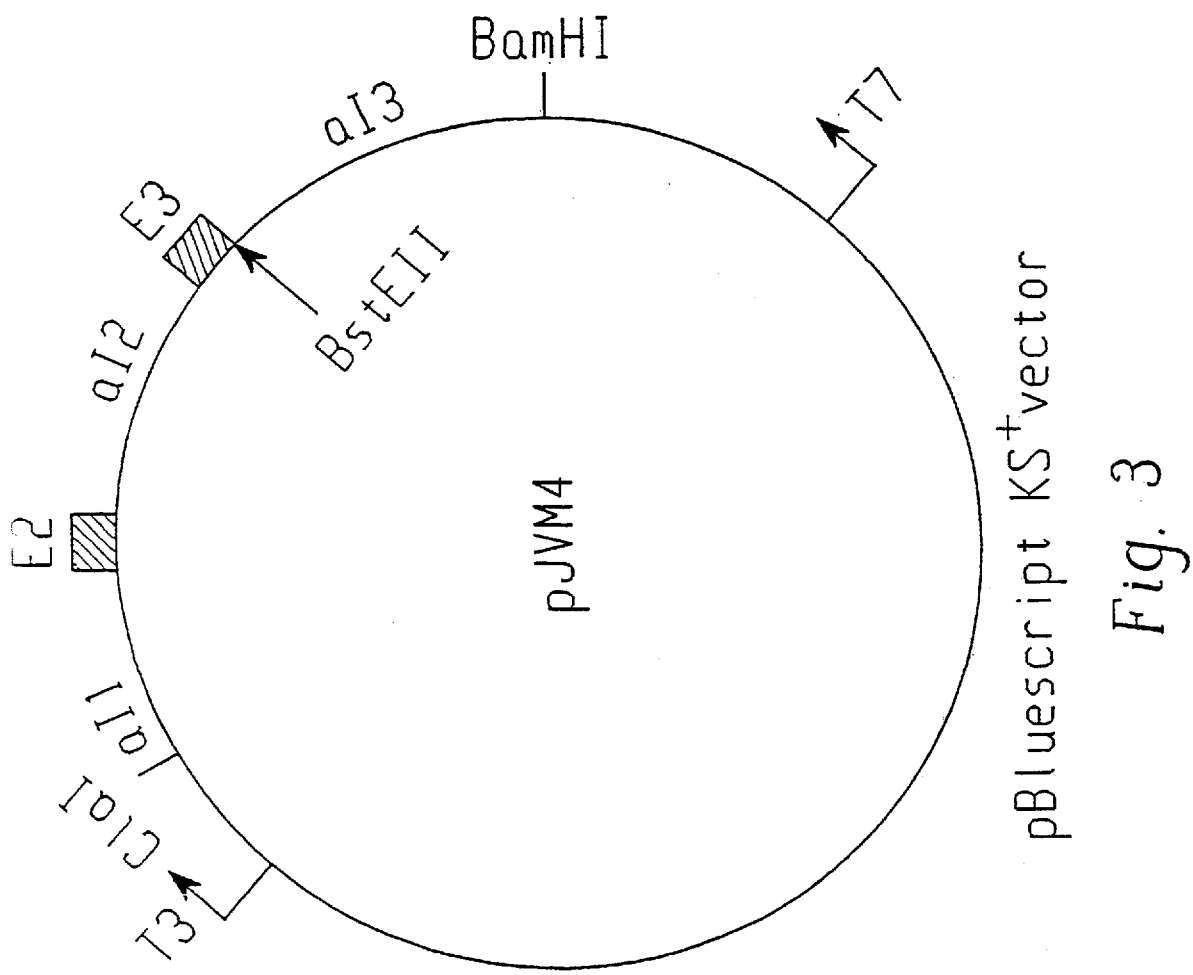
FIG. 3 is a diagram of the plasmid map of plasmid pJVM4.

The exogenous RNA was made by in vitro transcription of the plasmid pJVM4 which includes a fragment of the yeast mitochondrial COX1 gene from the ClaI site of the group II intron 1 (aI1) to the BamHI site of aI3 that has been inserted into the pBLUESCRIPT KS+plasmid. As shown in FIG. 3, which depicts the plasmid map of pJVM4, plasmid pJVM4 contains the following COX1 sequences: Exon 2, aI2, Exon 3 and parts of aI1 and aI3 sequence. The sequences are operably linked to a T3 RNA polymerase promoter. The Exon 2 and Exon 3 sequence are required for self-splicing of the aI2 intron RNA from the RNA transcript. pJVM4 was linearized with BstEII, which cuts at the 3' end of Exon 3 then 3 µg of the plasmid was incubated in 300 µl of 40 mM Tris-HCl at pH 8.0, 25 mM NaCl, 8 mM $MgCl_2$ 2 mM spermidine, 5 mM DTT 200 µM rNTPs, 182 U of RNasin from US Biochemical and 750 U of T3 RNA polymerase from BRL at 37° C. for 2 hours to make the RNA transcripts. Following the incubation, the RNA transcripts were phenol extracted, purified on G-50 column, phenol extracted and precipitated with ethanol. The RNA transcripts were then incubated in 40 mM Tris-HCl at pH 7.5, 100 mM $MgCl_2$, 2M $NH_4Cl$ at 40°–45° C. for 1 hour to allow self-splicing of the aI2 intron RNA molecules from the RNA transcripts and to obtain the splicing products. The splicing products, which include the excised aI2 RNA transcript, the ligated transcript which lacks the aI2 intron RNA, and the unspliced transcript, were desalted by passing through a G-50 column, then phenol extracted and ethanol precipitated to provide the exogenous RNA. The exogenous RNA was then resuspended to a final concentration of 1.0 µg/µl in 10 mM Tris-HCl, pH 8.0, 1 mM EDTA. A portion of the exogenous RNA was denatured by heating to 90° C. for 2 minutes and then immediately put on ice.

To prepare the reconstituted RNP particle preparation, 1 µl of the denatured exogenous RNA was added to 2 µl of the $1°2^{\Delta d5}$ RNP preparation (0.025 $O.D._{260}$ units) on ice for 2 minutes. The preparation was used immediately.

Example 12a
Purified Reconstituted Particles

Reconstituted particles are purified from reconstituted preparation of Example 12 according to the method of 1a.

Example 13
RNP Particle Preparation

An RNP particle preparation in which the group II intron RNA of the RNP particle has a "modified" EBS sequence that is complementary to a selected sequence on an intended single strand DNA substrate is prepared by two methods. First, oligonucleotide-directed mutagenesis of the group II intron DNA is performed by standard, well-known methods to change the nucleotides which encode the EBS sequences of the group II intron RNA. These sequences are in domain I of the group II intron RNA. The mutagenized intron DNA is then inserted into a vector, such as a plasmid, where it is operably linked to an RNA polymerase promoter, such as a promoter for T7 RNA polymerase or SP6 RNA polymerase or T3 RNA polymerase and an in vitro transcript of the modified group II intron RNA is made as described in example 12. The modified exogenous RNA transcript is then combined with an RNA-protein complex that has been isolated as described in example 12 to provide a modified reconstituted RNP particle preparation.

Alternatively, an RNP particle preparation in which the EBS sequences of the group II intron RNA are modified is prepared by site-directed mutagenesis of an organism, such as a yeast, as described in examples 3–9, and by isolation of the modified RNP particle preparation from the organism as described in example 1.

Example 13a
Purified Modified EBS Reconstituted Particles

RNP particles in which the EBS sequences of the group II intron RNA have been modified are purified from the preparation of Example 13 according to the method of 1a.

Example 14

An RNP particle preparation containing an RNP particle in which the loop region of domain IV of the group II intron RNA is modified, that is the loop region nucleotide sequence of domain IV differs from the nucleotide sequence of the aI2 RNA of Examples 1–10 is prepared by two methods. First oligonucleotide-directed mutagenesis of the aI2 intron DNA is performed by standard, well-known methods to change the nucleotide sequences which encode for the loop region of domain IV of the aI2 intron RNA. The mutagenized aI2 intron DNA is then inserted into a vector, such as a plasmid, where it is operably linked to an RNA polymerase promoter, such as a promoter for T7 RNA polymerase or SP6 RNA polymerase or T3 RNA polymerase and an in vitro transcript of the modified group II intron RNA made as described above in example 12. The exogenous RNA is then combined with an RNA-protein complex that has been isolated as described for example 12 to produce a modified reconstituted RNP particle preparation.

Alternatively, an RNP particle preparation in which the EBS sequences of the group II intron RNA are modified is prepared by site-directed mutagenesis of an organism, such as a yeast, as described in examples 4–10, and by isolation of the RNP particle preparation from the organism as described in example 1. IV is performed as in examples 4–10 of the aI2 intron DNA.

Example 14a
Purified Reconstituted Particles

Modified RNP particles are purified from the preparation of Example 14 according to the method of 1a.

Comparative Examples

Comparative Example A

A ribonucleoprotein preparation was isolated from the mitochondria of the mutant yeast strain $1°2°$, according to the protocol described in Example 1 to produce Comparative Example A. The mitochondrial COX1 gene of mutant yeast strain $1°2°$ lacks the aI1 and aI2 introns. Thus, the RNP preparation of Comparative Example A lacks excised aI1 RNA, excised aI2 RNA, and the proteins encoded by aI1 and aI2.

Comparative Example B

An RNP preparation was isolated from mutant yeast strain $1°2^{\Delta D5}$ according to the protocol described in Example 1 to produce Comparative Example B. The RNP preparation of Comparative Example B contains an aI2-encoded protein but lacks excised aI2 RNA.

Comparative Example C

An RNP preparation was isolated from the mitochondria of mutagenized yeast strain $1°2^{x4}$ according to the protocol described in Example 1 to produce Comparative Example C. The mutant allele $1°2^{x4}$ was obtained from Dr. Philip S. Perlman. The mutant allele was constructed by site-directed mutagenesis of pJVM16 and has the following changes in the aI2 intron: positions 2004–2012 changed from AAATTCGGT to GCAGCTGCT ($K_{668}F_{669}G_{670}$ to AAA). The RNP preparation of comparative example C contains a modified, excised aI2 RNA and an aI2-encoded protein that has a missense mutation in domain X.

Comparative Example D

An RNP preparation was isolated from the mitochondria of mutagenized yeast strain $1°2^{\Delta Zn}$ to produce comparative Example D. The mutant allele $1°2^{\Delta Zn}$ was obtained from Dr. Philip S. Perlman. The mutant allele was constructed by site-directed mutagenesis of pJVM16 and has the following change in the aI2 intron: positions 2028–2036 changed from CCTCATTCA to TAATAATAA ($P_{676}H_{677}S_{678}$ to OchOchOch). The RNP preparation of comparative example D contains a modified, excised aI2 RNA and an aI2-encoded protein that lacks the Zn domain.

Preparation of Substrate DNA

For methods in which it is desired that the nucleotide integrase function as a tool for cleaving double-stranded DNA substrate, it is highly preferred that the DNA substrate have a recognition site that is complementary to the hybridizing region of the group II intron RNA of the nucleotide integrase. When such recognition site is not present in the intended substrate, it is preferably added to the substrate. Examples of substrates to which a recognition site has been added are described below. Of course, where the nucleotide integrase is being used to characterize DNA substrates or to determine if the DNA contains certain target sequences, a recognition site is not added to the DNA substrate.

Plasmid pE2E3

Plasmid pE2E3 was made by cloning a 71 base pair insert consisting of the yeast mitochondrial COX1 exons 2 and 3 into the SmaI site of pbluescript KS+, obtained from Stratagene, La Jolla, Calif. to produce a 3032 base pair plasmid containing the target sequence 5'TTTTAGTAGCTGGTCATGCTGTAT-TAATAATTTTCTTCTTAGTAATGCCTGCTTTAATAGGAGGTTTTGGT), SEQ. ID. NO. 5, in the sense strand. The insert was generated from the mitochondrial DNA of yeast strain $1°2°$ by PCR using the primers E2-GII-O (5'TTTTAGTAGCTGGTCAGCTGTATT), SEQ. ID. NO. 12, and E3-GII-O (5'ACCAAAACCTCCTATTAAAGCAGGC), SEQ. ID. NO. 13. The insert differs from wild-type 161 sequence at three positions: T to C at position 10 of exon 2, G to A at position 29 of exon 2, and T to A at position 23 of exon 3.

Plasmid pE1E2

Plasmid pE1E2 was made by cloning a 105 base pair insert consisting of a portion of exon 1 and all of exon 2 of the yeast mitochondrial COX1 gene into the SmaI site of pBluescript KS+, obtained from Stratagene to produce a 3066 base pair plasmid. The insert was generated from the mitochondrial DNA of yeast strain m161/m161 C1036 delta 1 delta 2 whose construction is described in Kennell et al., 1993, by using the primers EIJY (5'TAATCAT TAGATTAGAATTAGCTGCACCTG), SEQ.ID.NO. 8 and E2JY (5'AGAAAATCATTAATACAGC), SEQ.ID. NO. 9.

Plasmid pJVM159

Plasmid pJVM159 was constructed as described in Kennell et al., 1993, Cell 73, 133–146. pJVM159 was obtained by cloning the 4.5 kb fragment of the yeast mitochondrial COX1 gene of strain $1^{+'}2°$ from an MspI site 217 nucleotides upstream of the start codon of exon 1 through the BamHI site in intron aI3 into pBluescript KS (+).

Double-Stranded 142 Base-Pair DNA Substrate from pE2E3

A 142 base pair double-stranded DNA substrate containing exons 2 and 3 of the yeast mitochondrial COX1 was generated from pE2E3 by PCR with the primers KS and SK. To prepare internally-labeled substrate, PCR was carried out in 25 μl of reaction medium containing 1 ng plasmid, 100 ng of each primer, 50 μCi [α-$^{32}$P]-dTTP (3,000 Ci/mmole) from DuPont NEN, Boston, Mass., 30 μM dTTP, 200 μM each of dATP, dCTP and dGTP and 2.5 units Taq DNA polymerase from Life Technologies for 25 cycles (94° C., 30 seconds; 55° C., 30 seconds; 72° C., 30 seconds). After PCR, the internally-labeled product was ethanol precipitated and purified in a 1.5% agarose gel, extracted with phenol-chloroform-isoamyl alcohol having ratio of 25:24:1 and then ethanol precipitated.

Double-Stranded 141 Base-Pair DNA Substrate from pE2E3

A similar 141 base pair internally-labeled double-stranded DNA substrate having a recognition site was synthesized from pE2E3 using primers T7 (5'GTAATACGACTCACTATAGGGC), SEQ. ID. NO. 10, and HG3 (5'CAAAAGCTGGGTACCGGGCCCCCCC), SEQ. ID. NO. 11. The PCR reactions were carried out as in the above paragraph. The amplified DNA substrate was digested with NotI and XhoI from Life Technologies, Inc. to remove 3' end heterogeneity resulting from PCR. The amplified DNA substrate was then ethanol precipitated and purified in a 1.5% agarose gel containing 90 mM Tris-borate, pH 8.3, 2 mM EDTA to provide a pE2E3-generated, internally-labeled, 141 base pair, double-stranded, linear DNA substrate.

5' End-labeled DNA Substrates from pE2E3

A 142 base pair double-stranded DNA substrate that was labeled on the 5' end of the sense strand was generated from pE2E3 by PCR with end-labeled primer SK (5'CGCTCTAGAACTAGTGGATC), SEQ.ID.NO.7, and unlabeled primer KS, both of which are complementary to a sequence in the polylinker. 0.2 μg of the primer SK was radiolabeled by using T4 polynucleotide kinase (New England Biolabs, Beverly, Mass.) and 150 μCi [γ-$^{32}$P]-ATP (3,000 Ci/mmole; DuPont (NEN). The PCR was carried out as in the above paragraph except in 100 μl of reaction medium with 4 ng plasmid template, 200 ng 5' end-labeled primer and 300 ng unlabeled primer. Following PCR, the labeled substrate DNAs were purified in a 1.5% agarose gel, extracted with phenol-chloroform-isoamyl alcohol (phenol-CIA; 25:24:1) and ethanol precipitated.

A 142 base pair double-stranded DNA substrate that was labeled on the 5' end of the antisense strand was generated from pE2E3 by PCR with 200 ng of the 5' end-labeled primer KS (5'TCGAGGTCG ACGGTATC), SEQ.ID.NO.6, and unlabeled primer SK, both of which are complementary to a sequence in the polylinker. 0.2 μg of primer KS was radiolabeled by using T4 polynucleotide kinase (New England Biolabs, Beverly, Mass.) and 150 μCi [γ-$^{32}$P]-ATP (3,000 Ci/mmole; DuPont (NEN). The PCR was carried out as in the above paragraph. Following PCR, the labeled substrate DNAs were purified in a 1.5% agarose gel, extracted with phenol-chloroform-isoamyl alcohol (phenol-CIA; 25:24:1) and ethanol precipitated.

3' End-labeled DNA Substrates from pE2E3

To prepare 3' end-labeled substrates, 1.25 μg of unlabeled PCR product generated from pE2E3 with primers SK and KS was digested with NotI or EcoRI, and the recessed 3' ends were filled in with [α-$^{32}$P]-dCTP or [α-$^{32}$P]-dTTP, respectively, and other unlabeled dNTPs by using Klenow DNA polymerase from Life Technologies, Inc. To ensure that only the desired 3' end was radiolabeled, the opposite end was then digested with EcoRI or BamHI.

Double-Stranded DNA Substrates from pE1E2

A 176 base pair internally-labeled double-stranded DNA substrate was synthesized from pE1E2 using primers SK and KS. The PCR reactions were carried out as for the internally labeled 142 basepan double-stranded DNA substrate. The amplified DNA substrate was ethanol precipitated and purified in a 1.5 agarose gel containing 90 mM Tris-borate, pH 8.3, 2 mM EDTA to provide a pE1E2-generated, double-stranded, linear DNA substrate.

5' End-Labeled Double-Stranded DNA Substrate From pE1E2

A 176 base pair double-stranded DNA substrate that was labeled on the 5' end of the sense strand was generated from pE1E2 by PCR with 200 ng of the primer SK that was 5' end-labeled using phage T4 polynucleotide kinase and [γ-$^{32}$P]-ATP (3,000 Ci/mmole; DuPont NEN). The PCR was carried out as in the above paragraph except in 100 μl of reaction medium with 4 ng plasmid template, 200 ng 5' end-labeled primer and 300 ng unlabeled primer. A 176 base pair double-stranded DNA substrate that was labeled on the 5' end of the antisense strand was generated from pE1E2 by PCR with 200 ng of the primer KS that was 5' end-labeled using phage T4 polynucleotide kinase and [γ-$^{32}$P]-ATP (3,000 Ci/mmole; DuPont NEN). The PCR was carried out as above in 100 μl of reaction medium with 4 ng plasmid template, 200 ng 5' end-labeled primer and 300 ng unlabeled primer SK.

Single-Stranded DNA Substrate from pE2E3

A 71 base-pair double-stranded DNA substrate having the recognition site was synthesized from plasmid pE2E3 by PCR with the oligonucleotides E2-GII-O (5'TTTTAGTAGCTGGTCAGCTGTATT), SEQ. ID. NO. 12, and E3-GII-O (5'ACCAAAACCTCCTATTAA AGCAGGC), SEQ). ID. NO. 13. The single stranded DNA substrate has the sequence 5'TTTTAGTAGCTGGTCAT-GCTGTATTAATAATTTTCTTCTTAG-TAATGCCTGCTTTAAT AGGAGGTTTTGGT), SEQ. ID. NO. 5, which is identical to the sense-strand of the double-stranded DNA substrate. The oligonucleotide was 3' end labeled with [α-$^{32}$P]-dTTP using terminal transferase from Life Technologies, Inc., according to the manufacturer's protocol. The labeled oligonucleotide was purified on a G-25 (Sigma) spin column, extracted with phenol-chloroform-isoamyl alcohol (phenol-CIA; 25:24:1), and ethanol precipitated. The specific activity was then adjusted to that of the double stranded DNA substrate by addition of unlabeled oligonucleotide.

Single-Stranded RNA Substrate

A 142 nucleotide RNA substrate was synthesized with phage T7 RNA polymerase from pE2E3 linearized with EcoRV. The RNA transcripts were synthesized in 25 μl of reaction medium containing 40 μCi [α-$^{32}$P]-UTP (3,000 Ci/mmol; DuPont NEN), 30 μM UTP, and 200 μM ATP, CTP and GTP. The RNA substrate was precipitated and purified in a denaturing 5% polyacrylamide gel. The labeling conditions were formulated so that the 3' exon of the RNA substrate has the same specific activity as the 3' exons of the DNA substrates derived from pE1E2.

Double-Stranded DNA from Neurospora crassa

A 180 base pair internally-labeled substrate was generated from Neurospora crassa strain 74A, which lacks the coI intron. The PCR reaction was carried out in 25 µl of reaction medium containing 1 ng mtDNA from strain 74A, 100 ng of the primer 5'GAGTTAAGCGGACCTGGGGTGCAG, SEQ ID. NO. 14, 100 ng of the primer 5'ATTAAGTCT TGGGAATGCCATGTC, SEQ No. 15, 40 µCi [$\alpha^{32}$P]dTTP (3000 Ci/mmol; DuPont NEN), 200 µM each of dATP, dCTP and dGTP, 2.5 U Taq DNA polymerase for 25 cycles of 94° C., 30 seconds; 55° C., 30 seconds; 72° C., 30 seconds. After PCR, the product was ethanol precipitated and gel-purified. The resulting substrate had the sense strand sequence of 5'GAGTTAAGCGGACCTGGGGTGCAGTA-CATTGCAGATAATCAATTATACAA TGC-TATAATAACTGCACATGCGATCTTAAT-GATTTTCTTTATGGTTATGCCAGCATTAATAGGTG GATTTGGTAATTTCTTGTTACCATTATTAGTAGGGG GTCCTGACATGGCATTCCCAAGACTTAAT, Seq.Id.No. 16.

Characterization of the RNP particle 0.3 O.D. $_{260}$ of the RNP particle preparations of examples 1 and 5 were applied to a 1% nondenaturing agarose gel in 90 mM Tris borate, pH 8.3, 2 mM EDTA at 4° C. and electrophoresed. The particles were transferred to a positively charged synthetic membrane from ICN by capillary transfer with 20×SSC which contains 3M NaCl, 0.3M Na-citrate at, pH 7.0. The membrane was rinsed at 4° C. in reaction buffer containing 50 mM Tris, pH 8.5, 100 mM KCl, 2 mM MgCl$_2$, 5 mM DTT with 0.05% Nonidet P-40 and 0.2% bovine serum albumin for 15 minutes. The membrane was then incubated for 15 minutes at 37° C. in 4 mL reaction buffer with 0.2% BSA 400 µCi [$\alpha$32P] dCTP (3000 Ci/mmol; DuPont NEN), and 0.2 mM each of dATP, dGTP and dTTP. The reaction was chased with 0.2 mM dCTP for 15 minutes at 37° C. Finally, the membrane was washed 3 times for 15 minutes in 10% trichloroacetic acid, 1% sodium pyrophosphate, and exposed for autoradiography.

The lane of the gel containing RNP particles of example 5 demonstrated a single radiolabeled band. The appearance of a single band indicated that the aI2 protein of example 5, which has reverse transcriptase activity, migrates as a particle in the nondenaturing gel in which it is associated with an endogenous RNA molecule which acts as a template. The aI2 protein specifically copies an aI2 RNA sequence and does not efficiently copy nonspecific RNA sequences. Kennell et al., 1993, Reverse transcriptase activity associated with maturase-encoding group II introns in yeast mitochondria. Cell 73, 133–146. Thus, the presence of a single band shows that the aI2 protein is associated with a specific aI2 RNA molecule. The RNP particles of example 1 did not produce a similar radiolabeled band. It is believed that this is due to an inhibition of endogenous reverse transcriptase activity in wild-type cells.

The RNP particles were resolved on a gel, blotted onto a membrane and probed with a radiolabeled RNA which is complementary to the aI2 RNA. This experiment showed that aI2 RNA with the size of excised aI2 RNA ran on the nondenaturing gel as a single band which co-migrated with the reverse transcription signal. Thus, the aI2 protein is associated in RNP particles with excised aI2 RNA.

A western blot was also prepared and showed that the aI2 protein that is present in the RNP particles of examples 1,2,4 5, 6,8, and 9 is a 62 kDa protein having reverse transcriptase function. Thus, the RNP particle which is isolated from the mitochondria of yeast strain $1°2^{+t}$ comprises an excised aI2 RNA and an associated 62 kDa aI2-encoded protein.

Cleaving Both Strands of a Double-Stranded DNA Substrate and Inserting an RNA Molecule into the Cleavage Site of One Strand Both strands of a double-stranded DNA substrate were cleaved at 37° C. and in a medium containing 100 mM KCl, 20 mM MgCl$_2$, 5 mM DTT, at pH 7.5, unless otherwise noted.

Cleaving both strands of the pE2E3-derived DNA Substrate and Inserting an RNA Molecule 465 fmoles (1,950,000 cpm) of the uniformly-labeled, 141 base pair DNA substrate were reacted with 0.375 O.D. units of the RNP particles of Example 1 in a volume of 150 µl. At 0, 1, 3, 5, 10, 20, and 30 minutes after reaction, 20 µl portions were removed and the reaction terminated by adding 80 µl of 10 mM EDTA, 0.3M NaOAc plus 2 µg linear acrylamide carrier, followed by extraction with phenol-chloroform-isoamyl alcohol (phenol-CIA; 25:24:1) and precipitation with ethanol. One-half of the precipitated products was treated with 0.1 µg RNase A from Sigma, St. Louis, Mo., in 50 µl of 10 mM Tris-HCl, pH 8.0, 1 mM EDTA for 15 minutes at 37° C. The products that had been treated with RNase A and the products that had not been treated with RNase A were then analyzed in a denaturing 6% polyacrylamide gel alongside a sequencing ladder generated from pE2E3 using the 5' end-labeled KS primer.

Only three bands were detected for the products that were not treated with RNAse A. These bands correspond to the 69 nucleotide 5' fragment of the antisense strand, the 72 nucleotide 3' fragment of the antisense strand and the 63 nucleotide 5' fragment of the sense strand of the DNA substrate. The missing 78 nucleotide product, corresponding to the 3' fragment of the sense strand, was detected only in those samples of DNA reaction products that were treated with RNase A prior to electrophoresis. These results indicate that the DNA substrate had been cleaved into four fragments and that an RNA molecule had been attached to the 3' fragment of the sense strand during reaction with the RNP particles.

Cleaving both strands of the pE2E3-derived DNA Substrate with RNP Particle Preparation of Examples 1, 2, 4 and 5

0.025O.D. $_{260}$ units of the RNP particle preparations of examples 1, 2, 4, 5 and comparative examples A–D were reacted with 125 fmoles (150,000 cpm) of the 142 base pair internally-labeled DNA substrate generated from pE2E3, for 20 minutes. To verify cleavage, the products were glyoxalated and analyzed in a 1% agarose gel.

A dark band of radiolabel of approximately 2.5 kb RNA was detected in the lanes containing the products that resulted from incubation of the DNA substrate with the RNP particles of Examples 1 and 2. A lighter band of RNA was detected in the lane containing the products that resulted from incubation of the DNA substrate with example 4, indicating that these RNP particles cleaved the sense strand of the substrate and catalyzed insertion of an RNA molecule into the cleavage site. The RNP particles of example 4 contain a mutated, excised aI2 intron RNA and an aI2-encoded protein which has a mutation in the reverse transcriptase domain. An even lighter band was detected in the lane containing products that resulted from incubation of the DNA substrate with the RNP particles of example 5, which contain a mutated, excised aI2 RNA and an aI2-encoded protein with a mutation in the Zn domain. No bands were detected in the lanes which contained the comparative examples. Thus RNP preparations which lack excised aI2 intron RNA or in which the intron-encoded protein lacks the nonconserved portion of the Zn domain, will neither cleave the DNA substrate nor attach an RNA.

Analyzing the DNA-RNA Reaction Products 625 fmoles (750,000 cpm) of the internally-labeled 142 base pair substrate DNA generated from pE2E3 were incubated with 0.125 O.D.$_{260}$ units of the RNP particles of Example 1 in 50 $\mu$l of medium containing 100 mM KCl, 20 mM MgCl$_2$, 50 mM Tris-HCl, pH 7.5, and 5 mM DTT at 37° C. for 20 minutes. Then 40 $\mu$l of 10 mM EDTA, 0.3M NaOAc and 2 $\mu$g linear acrylamide were added to the incubation mixture. The reaction products were extracted with phenol-CIA and precipitated with ethanol. The precipitated reaction products were divided into five portions and four of the portions were further treated with RNase A, alkali, S1 nuclease or DNase I. RNase A digestion was with 0.1 $\mu$g RNase A (Sigma, St. Louis, Mo.) in 50 $\mu$l of 10 mM Tris-HCl, pH 8.0, 1 mM EDTA for 15 minutes at 37° C. S$_1$ nuclease digestion was with 8 units S$_1$ nuclease in 50 $\mu$l of 30 mM NaOAc, pH 4.6, 50 mM NaCl, 1 mM ZnCl$_2$, and 1 $\mu$g single-stranded DNA (salmon sperm; Sigma) for 30 minutes at 25° C. DNase I digestion was with 7.5 units DNase I (Pharmacia, Piscataway, N.J.) in 50 $\mu$l of 100 mM NaOAc, pH 4.6, 5 mM MgCl$_2$ for 30 min at 37° C. Alkali treatment was with 50 $\mu$l of 0.1N NaOH at 50° C. for 1 hour, followed by ethanol precipitation in the presence of 0.3 mM NaOAc at pH 5.2. The reactions products were then glyoxylated and analyzed in a 1% agarose gel containing 10 mM sodium phosphate, pH 7.0 followed by autoradiography of the dried gel.

The gel revealed two closely spaced bands of about 2.5–2.7 kb RNA in the lane containing the products that resulted from incubation of the DNA substrate with the RNP particles. These bands were absent from the lanes containing substrate alone. These bands were also absent from the lanes containing products that had been treated with nucleases or alkali. Thus the 2.5 kb RNA was attached to the DNA substrate during the reaction. The finding that the RNA-DNA products withstand denaturation with glyoxal indicates a covalent linkage.

Cleavage of 3' and 5' end labeled DNA 0.025 O.D.$_{260}$ of the RNP particles of Example 1 were incubated for 20 minutes with 150,000 cpm of each of the 5' and 3' end-labeled DNA substrates generated from pE2E3, corresponding to 250 fmoles of 5' end-labeled substrates and 200 fmoles of 3' end-labeled substrates. To verify cleavage, the products were denatured with glyoxal and analyzed in a 1% agarose gel.

Two closely spaced dark bands of RNA were detected only with the substrate labeled at the 3' end of the sense strand. This indicates that both bands result from the ligation of the aI2 RNA to the 3' fragment of the sense strand. When the gels were exposed for a longer time, a lighter band was detected with the substrate that had been labeled at the 5' end of the sense strand. This indicates that a portion of the aI2 RNA is fully integrated into the cleavage site of the sense strand during the 20 minute incubation.

To confirm that the RNP particle preparation catalyzed the full integration of the RNA molecule into the cleavage site of the sense strand of the substrate, the radiolabeled products were eluted from the gel, subjected to reverse transcriptase-PCR, and sequenced. The PCR products included the sequence of exon 2 of the yeast mitochondrial COX1 gene followed by the sequence of the aI2 intron. Thus, the nucleotide integrase preparation catalyzed attachment of the excised aI2 RNA molecule to both fragments of the sense strand, i.e. full integration of the aI2 RNA molecule into the sense-strand cleavage site.

Identifying the RNA in the RNA-DNA Reaction Product

To confirm that the aI2 intron RNA is attached to the cleaved strand of the DNA substrate, oligo-directed Rnase H digestions were performed. For this analysis, oligonucleotides complementary to aI2 RNA were hybridized to an RNA sequence, and the sample was subjected to RNase H digestion which digests RNA in a RNA-DNA hybrid, but not single-stranded RNA. 0.025 O.D.$_{260}$ of the products were isolated on a 1% native agarose gel and eluted. After precipitation, the products, corresponding to 0.025 O.D.$_{260}$ starting materials, were combined with 40 ng each of one or more oligonucleotides in 10 $\mu$l of 40 mM Tris, pH 7.3, 100 mM KCl and 2 mM DTT. The products were heated to 90° C. for 2 minutes to denature the RNA and cooled on ice. 1 $\mu$l 100 mM MgCl$_2$, 0.5 $\mu$l RNasin (5 U) and 0.5 $\mu$l RNase H (1.4 U) were added, and the mixture was incubated for 30 minutes at 37° C. After phenol-CIA extraction and precipitation, the samples were glyoxalated and resolved on an agarose gel. The four oligonucleotides were found individually and in combination to result in a shift of migration of the products. In contrast, oligonucleotides which are complementary to exon 1, or to aI3 did not shift the migration of the products. Thus, the aI2 RNA is attached to the DNA substrate during the reaction.

Separate studies on a polyacrylamide gel, using an in vitro transcript of the aI2 RNA confirmed that both the 2.5 kb RNA-DNA product and the 2.7 kb RNA-DNA product represent two different forms of an aI2 RNA lariat attached to the cleaved fragment of the sense strand of the DNA substrate.

Identifying Nucleic Acid Sequences in Substrate DNA

The nucleotide integrase is useful to identify the presence of particular target sites in a double stranded substrate DNA or to cleave a double stranded substrate DNA which is known to possess the target site.

0.025 O.D.$_{260}$ units of the RNP particles of examples 1 and 2 were incubated for 20 minutes with 125 fmoles (150,000 cpm) of 3' end-labeled double-stranded DNA substrate derived from pE2E3 which contains the target sequence 5'TTTTAGTAGCTGGTCATGCTGTAT-T A A T A A T T T C TTCTTAGTAATGCCTGCTTTAATAGGAGGTTTTGGT), SEQ. ID. NO. 5, in the sense strand substrates. The products were extracted with CIA-phenol, ethanol-precipitated, glyoxylated and analyzed on 1% agarose gels.

A dark radiolabeled band of 2.5 kb RNA was detected in the products that resulted from the reaction between the RNP particles and the DNA that contained SEQ. ID. No. 5. A radiolabeled band was not detected in products resulting from incubation of RNP particles with a substrate that lacked the target sequence, or with a substrate lacking the sequence upstream of the putative cleavage site, ie. nucleotides 1–35 or with a substrate which contained the aI2-E3 junction of the COX1 gene. Only a faint radiolabeled band was detected when the RNP particles were incubated with a modified substrate which contains a 4 base pair substitution in IBS, or with a modified substrate that contained a 10 base pair insert at the putative cleavage site, i.e. between nucleotides 36 and 37, with a substrate that lacked nucleotides 37–71, or with a substrate that contained the E2-aI1 junction from the COX1 gene.

Thus the hybridizing IBS sequences in the substrate DNA are necessary for cleavage of the sense strand of the DNA substrate by the nucleotide integrase of examples 1 and 2. These results also indicate that the presence of additional sequences downstream of the cleavage site in the DNA substrate will impair cleavage of the substrate by the RNP particles of examples 1 and 2.

Cleaving both strands of the pE2E3-derived DNA Substrate and Inserting an RNA Molecule into the Cleavage Site of the Sense Strand Using the Purified RNP Particles 125 fmoles (150,000 cpm) of the internally-labeled 142 base pair substrate DNA generated from pE2E3 were incubated with 10 μl of each of the fractions obtained from the sucrose gradient in Example 1a. Taking into account the composition of the fractions, the final reaction medium of 20 μl contained 100 mM KCl, 20 mM $MgCl_2$, 50 mM Tris-HCl, pH 7.5, and 5 mM DTT. Following a 20 minute reaction at 37° C. for 20 minutes, 30 μl of water, 5 μl 0.3M NaOAc and 5 μg tRNA were added to the fractions. The reaction products were extracted with phenol-CIA and precipitated with ethanol, glyoxalated and analyzed on a 1% agarose gel containing 10 mM sodium phosphate, pH 7.0 followed by autoradiography of the dried gel. The radiolabeled bands at 2.5 kb were quantified with a Molecular Dynamics Phosphorimager.

Radiolabeled bands of 2.5 kb were detected when the DNA substrate was reacted with each of the fractions. Thus, the purified RNP particles of example 1a are used to cleave both strands of a double-stranded DNA substrate and to insert the aI2 intron RNA into the cleavage site.

Cleaving Both Strands of a pE2E3 derived double-stranded DNA substrate with the Reconstituted RNP Particle Preparation and with the RNP Preparation of Example 10

The reconstituted RNP particle preparation of Example 12 was reacted with 250 fmoles (300,000 cpm) of the 142 base pair DNA substrates generated from pE2E3 and which were 5' end-labeled on either the sense strand or the antisense strand for 20 minutes at 37° C. To verify cleavage of both strands of the substrate, the reaction products were extracted with phenol-CIA in the presence of 0.3M NaOAc and 2 μg single-stranded salmon sperm DNA followed by precipitation with ethanol. DNA reactions products were analyzed in a 6% polyacrylamide/8M urea gel, alongside dideoxy sequencing ladders generated from pE2E3 using 5' end-labeled primers KS or SK.

Radiolabeled bands of DNA corresponding to the 5' fragment of the sense strand and to the 5' fragment of the antisense strand were detected for the products resulting from reaction of reconstituted particle preparation and the 5' end-labeled DNA substrates. Thus the reconstituted particle preparation cleaves both strands of the DNA substrate derived from pE2E3. Similar results, i.e. cleavage of both strands, were obtained when the 5' end labeled substrates were incubated with the RNP particle preparation of example 10.

Cleaving both strands of DNA Substrate Derived from pE1E2 and Inserting an RNA Molecule into the Cleavage Site of the Sense Strand 100 fmoles (150,000 cpm) of the internally-labeled pE1E2-derived substrate were incubated with 0.025 $O.D._{260}$ of the RNP particle preparations of either Example 1 or Example 2 in a medium containing 50 mM KCl, 10 mM $MgCl_2$, 50 mM Tris-HCl at pH 7.5, and 5 mMDTT for 20 minutes. A portion of the DNA incubation products were digested with nucleases. The incubation products were extracted with phenol-CIA and precipitated with ethanol. The DNA incubation products were glyoxylated and applied to a 1% agarose gel containing 10 mM sodium phosphate at pH 7.0. The gel was electrophoresed and dried. The dried gel was autoradiographed.

Two radiolabeled bands of approximately 2.5 kb RNA were detected on the gel when the DNA substrate was incubated with the RNP particles of Example 1. These bands were not detected for the incubation products that were treated with RNase A or alkali. These results indicate that the excised aI1 RNA molecule of approximately 2.5 kb, was attached to the 176 base pair DNA substrate during incubation with the RNP particles of example 1. Radiolabled bands were not detected when substrate DNA was incubated with the RNP particles of Example 2.

Cleavage of End Labeled DNA Substrates

To further characterize the DNA-RNA products, 0.025 $O.D._{260}$ of the RNP particles of example 1 were incubated with 150,000 cpm of each of the 5' and 3' end-labeled DNA substrates generated from pE1E2, corresponding to 250 fmoles of 5' end-labeled substrates and 200 fmoles of 3' end-labeled substrates. Following a 20 minute incubation, the products were denatured with glyoxal and analyzed in a 1% agarose gel.

Radiolabeled bands of approximately 2.5 kb RNA were detected when the RNP particles were incubated with the 5' and 3' end-labeled DNA substrates which indicated that a complete integration of the RNA molecule into the cleavage site of the sense strand had occurred. Radiolabeled bands were not detected when the RNP particles of example 1 were incubated with substrate that had been radiolabeled on either the 5' end or the 3' end of the antisense strand of the substrate DNA.

Analyzing the RNA-DNA Product formed by reaction of the pE1E2 derived DNA substrate with Nucleotide Integrase The products that resulted from reacting an internally-labeled pE1E2-derived substrate with the RNP particles of Example 1 were further analyzed on a denaturing 3.5% polyacrylamide gel (39:1 acrylamide-bisacrylamate), using an excised aI2 RNA molecule as a marker. Three bands were detected on the autoradiograph of the gel. The location of the two, slower-migrating bands suggested that they represented a radiolabeled 3' sense-strand fragment attached to an aI1 lariat RNA molecule, while the location of the third, faster-migrating band was consistent with the migration of a linear molecule with the length of aI1. Since reacting the RNP particles of example 1 with a 5' end labeled substrate derived from pE1E2 also results in this band, it indicates that the reaction results in a complete integration of the aI1 RNA into the cleavage site of the sense strand.

Next, to confirm that the RNP preparation of example 1 catalyzed the full integration of the RNA molecule into the cleavage site of the sense strand of the substrate, the radiolabeled products were eluted from the gel. The products were subjected to reverse transcriptase-PCR in which the eluted RNA was first reverse transcribed using a primer complementary to aI1 RNA. The resulting cDNA amplified by PCR using one primer complementary to the RNA sequence and one primer complementary to the vector. The PCR products were gel purified, cloned into pKS (+) digested with Sma 1 and sequenced according the method of Sanger. The PCR products included the sequence of exon 1 of the yeast mitochondrial COX1 gene followed by the sequence of the aI1 intron. The PCR products also included the sequence of the aI2 intron followed by the sequence of exon 2 of the yeast mitochondrial COX1 gene. Thus, the nucleotide integrase catalyzed attachment of the RNA molecule to both fragments of the sense strand, i.e. full integration of the RNA molecule into the sense-strand cleavage site.

Cleaving Both Strands of a Double-Stranded DNA Substrate and Inserting RNA into the cleavage site of one DNA strand and a cDNA into the Cleavage Site of the Second Strand The nucleotide integrases that cleave both strands of double stranded DNA and insert an RNA into the cleavage site of one strand are also employed in the method for inserting cDNA in the second strand. The method for inserting the cDNA into the second strand is quite similar to the method for cutting the two strands and inserting an RNA except where a cDNA is desired deoxynucleotides must be present in the reaction mixture.

Cleavage of Substrate pJVM159 and Attachment of a cDNA 0.025 O.D.$_{260}$ units of the RNP particle preparations of examples 1, 2, 4 and 5 and of the materials of comparative Examples A and B were combined with 1 µg of plasmid pJVM159 in 10 µl of reaction medium. The reaction medium contained 0.2 mM each of dATP, dGTP and dTTP, 10 µCi [α-$^{32}$P]-dCTP (3,000 Ci/mmole; DuPont NEN, Boston, Mass.), 100 mM KCl, and 5 mM dithiothreitol, 2 mM MgCl$_2$, and 50 mM Tris-HCl, pH 8.5. The reaction was initiated by addition of the RNP preparations, incubated for 10 minutes at 37° C., and chased with 0.2 mM dCTP for another 10 minutes. After the chase period, the reactions were terminated by extraction with phenol-CIA (phenol-chloroform-isoamyl alcohol; 25:24:1) in the presence of 0.3M sodium acetate, pH 7.8, and 5 µg E. coli tRNA carrier (Sigma, St. Louis, Mo.). Products were ethanol precipitated twice and resolved in 1% agarose gels containing 90 mM Tris-borate, pH 8.3, 2 mM EDTA and 0.05% ethidium bromide. The gels were dried and autoradiographed.

Two additional radiolabeled bands were detected in the lanes containing the products that resulted from incubation of the substrate DNA and the RNP particles of examples 1 and 2, as compared to the control which lacked substrate DNA. This result indicates that the RNP particles of examples 1 and 2 catalyze the formation of a DNA molecule on the cleaved DNA substrate. Such additional bands were not detected when the substrate was incubated with the material of comparative example A, with the RNP particles of Example 4, with the RNP particles of example 5 or the material of comparative example B. Thus, a nucleotide integrase which lacks an excised group II intron RNA or which contains a group II intron-encoded protein that lacks a reverse transcriptase domain does not catalyze the formation of a cDNA molecule on the cleaved strand.

Cleavage of pE2E3 substrate and attachment of a cDNA

Four µg of plasmid pE2E3 were reacted with 0.100 O.D.$_{260}$ units of the RNP particle preparation of example 1 in 40 µl of reaction medium containing 0.2 mM each of dATP, dGTP and dTTP, 40 µCi [α-$^{32}$P]-dCTP (3,000 Ci/mmole; DuPont NEN, Boston, Mass.), 100 mM KCl, 5 mM dithiothreitol, 5 mM MgCl$_2$, and 50 mM Tris-HCl, pH 7.5. The reaction was initiated by addition of the RNP particle preparations, incubated for 10 minutes at 37° C., and chased with 0.2 mM dCTP for another 10 minutes. The reaction products were phenol extracted, precipitated and divided into four parts. One part was incubated for 15 minutes at 37° C. in 50 µl of low salt buffer containing 0.1 µg RNase A from Sigma, 10 mM Tris-HCl, pH 8.0, and 1 mM EDTA. Another part was incubated for 30 minutes at 37° C. in 50 µl of medium containing 2.7 units RNase H from Life Technologies, Inc., 100 mM KCl, 10 mM MgCl$_2$, 20 mM Tris-HCl, pH 7.5, and 0.1 mM DTT. The products were extracted with phenol-CIA (phenol-chloroform-isoamyl alcohol; 25:24:1) in the presence of 0.3M sodium acetate at pH 7.8, and 5 µg E. coli tRNA carrier (Sigma, St. Louis, Mo.), ethanol precipitated twice and resolved in 1% agarose gels containing 90 mM Tris-borate, pH 8.3, 2 mM EDTA and 0.05% ethidium bromide. The gels were dried and autoradiographed.

RNase A digestion of the $^{32}$p-labeled plasmid products carried out under low salt conditions to degrade both single stranded and double-stranded RNA, reduced most of the $^{32}$P-labeled products to a single predominant band, which migrated close to linear pE2E3. This most likely resulted from removal of the RNA template. RNase H, which is specific for RNA-DNA duplexes, also increased the mobility of the $^{32}$P-labeled products, which indicates that the template RNA is based paired to DNA.

Dideoxy-sequencing of the products showed that the first nucleotide incorporated was the A residue ten nucleotides downstream of the intron RNA insertion site. i.e., cDNA formation began at the antisense strand cleavage site. The sequencing ladders of the longer cDNAs showed that the 3' OH of the 5' fragment of the antisense strand is used as the primer for the formation of the cDNA and that the cDNA synthesis is initiated just downstream of the intron RNA and extends into domain VI of the intron RNA.

Cleaving One Strand of Double-Stranded DNA With the RNP Particles of Examples 6, 7, 8, and 9

0.025O.D.$_{260}$ units of the RNP particles from examples 1,2,4,5,6,7,8,9, and of the material of comparative examples A–D were incubated with 250 fmoles (300,000 cpm) of the 142 base pair DNA substrates that were generated from pE2E3 and which were 5' end-labeled on either the sense strand or the antisense strand. For comparison, the 5' end labeled DNA substrate was also incubated the RNP particle preparation of Example 1 that had been boiled prior to incubation, or had been treated with 1 µg of RNase A at 37° C. for two minutes prior to incubation, or had been treated with 1 µg of protease K at 37° C. for 2 minutes prior to incubation. Following a 20 minute incubation at 37° C., and the DNA incubation products were extracted with phenol-CIA in the presence of 0.3M NaOAc and 2 µg single-stranded salmon sperm DNA followed by precipitation with ethanol. DNA incubation products were analyzed in a 6% polyacrylamide/8M urea gel, alongside dideoxy sequencing ladders generated from pE2E3 using 5' end-labeled primers KS or SK.

A radiolabeled band corresponding to the 5' fragment was detected when RNP particles of examples 1 and 2 were incubated with substrates that had been labeled on the 5' end of either the sense strand or the antisense strand of the DNA substrate, indicating that these particles cleaved both strands of the DNA substrate. The RNP particles of Example 1 cleaved the sense strand precisely at the exon 2-exon 3 junction of the sense strand. The RNP particles of examples 1 and 2 cleaved the antisense strand 10 base pairs downstream from the sense strand cleavage site. RNP particles of Example 1 that had been treated with protease K, or RNase A, or boiled did not cleave either strand.

Radiolabeled bands were also detected when the RNP particles of Example 4 were incubated with DNA substrates that had been 5' end-labeled on either the sense strand or antisense strand, indicating that this nucleotide integrase cleaved both strands of DNA substrate. The RNP particles of example 4 contain a modified, excised aI2 RNA and an aI2-encoded protein which lacks detectable reverse transcriptase activity. Although the extent of cleavage of RNP particles of Example 4 is somewhat reduced compared to cleavage with the RNP particle preparation of Example 1, the endonuclease activity of the RNA is present even when the reverse transcriptase activity of the aI2-encoded protein is absent.

The radiolabeled bands were detected when the RNP particles of Example 5 were incubated with the DNA substrate that had been labeled on the 5' end of either the sense strand or antisense strand. In quantitative assays normalized by either O.D.$_{260}$ or soluble aI2 reverse transcriptase activity, the cleavage activities for the antisense and sense strands by the RNP particles of Example 5 were 6% and 25%, respectively, of activities of the RNP particles of Example 1.

A radiolabeled band corresponding to the 5' fragment was detected when the DNA substrate labeled on the 5' end of the sense strand was incubated with the RNP particles of example 6, but a band corresponding to the 5' fragment of the sense strand was not detected when the RNP particles of example 6 were incubated with a DNA substrate that had been labeled on the 5' end of the antisense strand. The RNP particles of example 6 contain a modified, excised aI2 intron RNA and an aI2-encoded protein that has an alteration in one of the putative endonuclease motifs. Similar results were obtained with the RNP particles of example 7, which contains a modified, excised aI2 intron RNA and an aI2-encoded protein in which the conserved portion of the Zn domain is absent. Likewise, RNP particles of examples 8 and 9, each of which contains a modified, excised aI2 intron RNA and an aI2-encoded protein in which there is a mutation in the $Zn^{2+}$-like motif, cleaved the sense strand but not the antisense strand of the DNA substrate. For the RNP particles of examples 6, 7, 8, and 9, the level of sense-strand cleavage was proportional to the amount of RNA-DNA products detected in the agarose gels. These findings indicate that the antisense strand endonuclease activity of the aI2-encoded protein is associated with the Zn domain.

Comparative Example B, which lacks excised aI2 RNA, and Comparative Example D, which contains an aI2-encoded protein that lacks the Zn domain, did not cleave either DNA strand.

A radiolabeled band corresponding to the 5' fragment was detected when the reconstituted RNP particle preparation of example 12 was incubated with substrates that had been labeled on the 5' end of either the sense strand or the antisense strand of the DNA substrate. These results establish that the reconstituted RNP particle preparation cleaves both strands of the DNA substrate.

Thus, both the catalytic RNA molecule of the nucleotide integrase and the intron-encoded protein are required for cleavage of both strands of the double stranded DNA. Certain modifications in the Zn domain and the X domain of intron-encoded protein disrupt the cleavage of the antisense strand of the nucleotide integrase. It is believed that the excised group II intron of the nucleotide integrase cleaves the first strand of the double-stranded DNA substrate and that the group II intron-encoded protein of the nucleotide integrase cleaves the second strand of the double-stranded DNA substrate.

Cleaving Single-stranded DNA Substrates

The RNP particle preparation of Example 1 was incubated with the following DNA substrates: 71 base pair internally-labeled double-stranded DNA derived from pE2E3; the 3' end-labeled 71 nucleotide single-stranded DNA derived from pE2E3; and an 142 nucleotide in vitro transcript of aI2 RNA. The incubation was conducted in a medium either containing 100 mM KCl, 20 mM $MgCl_2$, 50 mM Tris-HCl, pH 7.5, and 5 mM DTT for 20 minutes at 37° C. or in the same reaction medium supplemented to 100 mM $MgCl_2$ for 1 hour at 37° C. The DNA and RNA incubation products were extracted with phenol-CIA in the presence of 0.3M NaOAc, pH 5.2 with 5 μg E. coli tRNA carrier from Sigma, and then ethanol precipitated and glyoxylated. The glyoxylated RNA and DNA products were then analyzed by electrophoresis in a 1% agarose gel and quantitated with a Molecular Dynamics phosphorimager.

Dark radiolabeled bands of approximately 2.5 kb and 2.7 kb RNA were detected for the products that resulted from incubation of the RNP particles with the double-stranded and single-stranded DNA substrates, in 20 mM $Mg^{2+}$. In contrast, only a very faint band was detected for the products that resulted from incubation of the RNP particles with the RNA substrate in 20 mM $Mg^{2+}$. Time course experiments showed that the relative rates of RNA insertion into the substrate by the RNP particle preparation at 20 mM $Mg^{2+}$ were 32.:62:1 for the double-stranded DNA, single stranded DNA and RNA, respectively. Thus, the preferred substrate for the nucleotide integrase is a double-stranded or single-stranded DNA substrate.

When the magnesium ion concentration of the medium was increased to 100 mM, only faint radiolabeled bands were detected for the products that resulted from incubation of the RNP particles with the double-stranded and single-stranded DNA substrates, which indicates that the insertion of an RNA molecule into the cleavage site of double-stranded DNA or single-stranded DNA works better at a $Mg^{2+}$ concentration below 100 mM.

Cleaving Substrate with IBS Recognition Site

The nucleotide integrase is useful to identify the presence of particular target sites in a single stranded substrate DNA or to cleave a single stranded substrate DNA which is known to possess the target site.

0.025 $O.D._{260}$ units of the RNP particles of example 1 were with the 3' end-labeled single stranded DNA substrate derived from pE2E3 that contained the target sequence, 5' T T T T A G T A G C T G G T C A T G C T G T A T TAATAATTTTCTTCTTAGTAATGCCTGCTTTAATAGG AGGTTTTGGT), SEQ. ID. NO. 5 and with three single stranded DNA substrates that contained modified target sequences. Following a 20 minute incubation, the products were extracted with CIA-phenol, ethanol-precipitated, glyoxylated and analyzed on 1% agarose gels.

A dark radiolabeled band of 2.5 kb of RNA was detected the products when the nucleotide integrase and double-stranded DNA substrate derived from pE2E3 which contains the target sequence. Similarly, a radiolabeled band was detected when the RNP preparations were incubated with a single-stranded substrate that contained either IBS3, nucleotides 31 to 36 of SEQ. ID No. 5 or that contained IBS4, nucleotides 25 to 30 of SEQ. ID NO. 5. In contrast, bands were not detected when the RNP preparations were incubated with a single-stranded DNA substrate that lacked both the IBS3 and IBS4 sequence. Thus the nucleotide integrase of example 1 is useful for cleaving single stranded DNA that contains the sequence TTTTCT or TTAATAA.

What is claimed is:

1. A method for making a reconstituted RNP particle preparation comprising the following steps:
   (a) providing an exogenous first RNA molecule which comprises an excised group II intron RNA and lacks flanking exon sequences, said group II intron RNA comprising a hybridizing region which is capable of hybridizing to a recognition site on a DNA substrate;
   (b) providing an RNA-protein complex comprising:
      (i) a protein having an amino acid sequence encoded by a group II intron, said protein comprising an X domain and a Zn domain, and
      (ii) a second RNA molecule; wherein said second RNA molecule is not an excised group II intron RNA having a sequence that encodes said protein; and wherein said second RNA molecule is bound to said protein to form said RNA-protein complex; and
   (c) combining said exogenous first RNA with said RNA-protein complex to form a reconstituted RNP particle that is capable of cleaving said DNA substrate, said reconstituted RNP particle comprising said first exogenous RNA molecule bound to said protein.

2. The method of claim 1 wherein the exogenous RNA comprises a yeast mitochondrial group II intron RNA and the protein comprises an amino acid sequence encoded by a yeast mitochondrial group II intron.

3. The method of claim 1 wherein the exogenous RNA comprises an excised RNA transcript that is encoded by the group II intron aI2 of the yeast mitochondrial COX1 gene and said protein comprises an amino acid sequence encoded by the group II intron aI2 of the yeast mitochondrial COX1 gene.

* * * * *

UNITED STATES PATENT AND TRADEMARK OFFICE
CERTIFICATE OF CORRECTION

PATENT NO. : 5,869,634
DATED : February 9, 1999
INVENTOR(S) : Alan M. Lambowitz, Steven Zimmerly, Jian Yang, and Huatao Guo It is certified that error appears in the above-identified patent and that said Letters Patent is hereby corrected as shown below:

In column 46, line 42, after "mitochondrial" please delete "COX1" and replace with -- *COX1* --.

In column 46, line 44, after "mitochondrial", please delete "COX1" and replace with -- *COX1* --.

Signed and Sealed this

First Day of June, 1999

Attest:

Q. TODD DICKINSON

*Attesting Officer*       *Acting Commissioner of Patents and Trademarks*

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 2483 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:1:

```
GTGCGCCGTT  TCGCTTAATT  TATCACTGTA  TTGAAGTGTT  AATTGATAAA  CATATCTCTG       60
TTTATTCAAT  TAATGAAAAC  TTTACCGTAT  CATTTTGGTT  CTGATTATTA  GTAGTAACAT      120
ACATAGTATT  TAGATACGTA  AACCATATGG  CTTACCCAGT  TGGGGCCAAC  TCAACGGGGA      180
CAATAGCATG  CCATAAAAGC  GCTGGAGTAA  AACAGCCAGC  GCAAGGTAAG  AACTGTCCGA      240
TGGCTAGGTT  AACGAATTCC  TGTAAAGAAT  GTTAGGGTT   CTCATTAACT  CCTTCCCACT      300
TGGGGATTGT  GATTCATGCT  TATGTATTGG  AAGAAGAGGT  ACACGAGTTA  ACCAAAAATG      360
AATCATTAGC  TTTAAGTAAA  AGTTGACATT  TGGAGGGCTG  TACGAGTTCA  AATGGAAAAT      420
TAAGAAATAC  GGGATTGTCC  GAAAGGGGAA  ACCCTGGGGA  TAACGGAGTC  TTCATAGTAC      480
CCAAATTTAA  TTTAAATAAA  GCGAGATACT  TTAGTACTTT  ATCTAAATTA  AATGCAAGGA      540
AGGAAGACAG  TTTAGCGTAT  TTAACAAAGA  TTAATACTAC  GGATTTTCC   GAGTTAAATA      600
AATTAATAGA  AAATAATCAT  AATAAACTTG  AAACCATTAA  TACTAGAATT  TTAAAATTAA      660
TGTCAGATAT  TAGAATGTTA  TTAATTGCTT  ATAATAAAT   TAAAAGTAAG  AAAGGTAATA      720
TATCTAAAGG  TTCTAATAAT  ATTACCTTAG  ATGGGATTAA  TATTTCATAT  TTAAATAAAT      780
TATCTAAAGA  TATTAACACT  AATATGTTTA  AATTTTCTCC  GGTTAGAAGA  GTTGAAATTC      840
CTAAAACATC  TGGAGGATTT  AGACCTTTAA  GTGTTGGAAA  TCCTAGAGAA  AAAATTGTAC      900
AAGAAAGTAT  GAGAATAATA  TTAGAAATTA  TCTATAATAA  TAGTTTCTCT  TATTATTCTC      960
ATGGATTTAG  ACCTAACTTA  TCTTGTTTAA  CAGCTATTAT  TCAATGTAAA  AATTATATGC     1020
AATACTGTAA  TTGATTTATT  AAAGTAGATT  TAAATAAATG  CTTTGATACA  ATTCCACATA     1080
ATATGTTAAT  TAATGTATTA  AATGAGAGAA  TCAAAGATAA  AGGTTTCATA  GACTTATTAT     1140
ATAAATTATT  AAGAGCTGGA  TATGTTGATA  AAAATAATAA  TTATCATAAT  ACAACTTTAG     1200
GAATTCCTCA  AGGTAGTGTT  GTCAGTCCTA  TTTTATGTAA  TATTTTTTA   GATAAATTAG     1260
ATAAATATTT  AGAAAATAAA  TTTGAGAATG  AATTCAATAC  TGGAAATATG  TCTAATAGAG     1320
GTAGAAATCC  AATTTATAAT  AGTTTATCAT  CTAAAATTTA  TAGATGTAAA  TTATTATCTG     1380
AAAAATTAAA  ATTGATTAGA  TTAAGAGACC  ATTACCAAAG  AAATATGGGA  TCTGATAAAA     1440
GTTTTAAAAG  AGCTTATTTT  GTTAGATATG  CTGATGATAT  TATCATTGGT  GTAATGGGTT     1500
CTCATAATGA  TTGTAAAAAT  ATTTTAAACG  ATATTAATAA  CTTCTTAAAA  GAAAATTTAG     1560
GTATGTCAAT  TAATATAGAT  AAATCCGTTA  TTAAACATTC  TAAAGAAGGA  GTTAGTTTTT     1620
TAGGGTATGA  TGTAAAAGTT  ACACCTTGAG  AAAAAAGACC  TTATAGAATG  ATTAAAAAAG     1680
GTGATAATTT  TATTAGGGTT  AGACATCATA  CTAGTTTAGT  TGTTAATGCC  CCTATTAGAA     1740
GTATTGTAAT  AAAATTAAAT  AAACATGGCT  ATTGTTCTCA  TGGTATTTTA  GGAAAACCCA     1800
GAGGGGTTGG  AAGATTAATT  CATGAAGAAA  TGAAAACCAT  TTAATGCAT   TACTTAGCTG     1860
TTGGTAGAGG  TATTATAAAC  TATTATAGAT  TAGCTACCAA  TTTTACCACA  TTAAGAGGTA     1920
GAATTACATA  CATTTTATTT  TATTCATGTT  GTTAACATT   AGCAAGAAAA  TTTAAATTAA     1980
```

| | | | | | | |
|---|---|---|---|---|---|---|
| ATACTGTTAA | GAAAGTTATT | TTAAAATTCG | GTAAAGTATT | AGTTGATCCT | CATTCAAAAG | 2040 |
| TTAGTTTTAG | TATTGATGAT | TTTAAAATTA | GACATAAAAT | AAATATAACT | GATTCTAATT | 2100 |
| ATACACCTGA | TGAAATTTTA | GATAGATATA | AATATATGTT | ACCTAGATCT | TTATCATTAT | 2160 |
| TTAGTGGTAT | TTGTCAAATT | TGTGGTTCTA | AACATGATTT | AGAAGTACAT | CACGTAAGAA | 2220 |
| CATTAAATAA | TGCTGCCAAT | AAAATTAAAG | ATGATTATT | ATTAGGTAGA | ATGATTAAGA | 2280 |
| TAAATAGAAA | ACAAATTACT | ATCTGTAAAA | CATGTCATTT | TAAAGTTCAT | CAAGGTAAAT | 2340 |
| ATAATGGTCC | AGGTTTATAA | TAATTATTAT | ACTATTAAAT | ATGCGTTAAA | TGGAGAGCCG | 2400 |
| TATGATATGA | AAGTATCACG | TACGGTTCGG | AGAGGGCTCT | TTTATATGAA | TGTTATTACA | 2460 |
| TTCAGATAGG | TTTGCTACTC | TAC | | | | 2483 |

(2) INFORMATION FOR SEQ ID NO:2:

(i) SEQUENCE CHARACTERISTICS:
        (A) LENGTH: 2448 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:2:

| | | | | | | |
|---|---|---|---|---|---|---|
| GTGCGCCTCT | CAGTGCGTAT | ATTTCGTTGA | TGCGTCTAGC | ATTAGTATTA | TGAATCATCA | 60 |
| ATAGATACTT | AAAACATATG | ACTAACTCAG | TAGGGGCTAA | CTTTACGGGG | ACAATAGCAT | 120 |
| GTCATAAAAC | ACCTATGATT | AGTGTAGGTG | GAGTTAAGTG | TTACATGGTT | AGGTTAACGA | 180 |
| ACTTCTTACA | AGTCTTTATC | AGGATTACAA | TTTCCTCTTA | TCATTTGGAT | ATAGTAAAAC | 240 |
| AAGTTTGATT | ATTTACGTT | GAGGTAATCA | GATTATGATT | CATTGTTTTA | GATAGCACAG | 300 |
| GCAGTGTGAA | AAAGATGAAG | GACCTAAATA | ACACAAAAGG | AAATACGAAA | AGTGAGGGAT | 360 |
| CAACTGAAAG | AGGAAACTCT | TGAGTTGACA | GAGGTATAGT | AGTACCGAAT | ACTCAAATAA | 420 |
| AAATGAGATT | TTTAAATCAA | GTTAGATACT | ATTCAGTAAA | TAATAATTTA | AAAATAGGGA | 480 |
| AGGATACCAA | TATTGAGTTA | TCAAAAGATA | CAAGTACTTC | GGACTTGTTA | GAATTTGAGA | 540 |
| AATTAGTAAT | AGATAATATA | AATGAGGAAA | ATATAAATAA | TAATTTATTA | AGTATTATAA | 600 |
| AAAACGTAGA | TATATTAATA | TTAGCATATA | ATAGAATTAA | GAGTAAACCT | GGTAATATAA | 660 |
| CTCCAGGTAC | AACATTAGAA | ACATTAGATG | GTATAAATAT | AATATATTTA | AATAAATTAT | 720 |
| CAAATGAATT | AGGAACAGGT | AAATTCAAAT | TTAAACCCAT | GAGAATAGTT | AATATTCCTA | 780 |
| AACCTAAAGG | TGGTATAAGA | CCTTTAAGTG | TAGGTAATCC | AAGAGATAAA | ATTGTACAAG | 840 |
| AAGTTATAAG | AATAATTTTA | GATACAATTT | TTGATAAAAA | GATATCAACA | CATTCACATG | 900 |
| GTTTTAGAAA | GAATATAAGT | TGTCAAACAG | CAATTTGAGA | AGTTAGAAAT | ATATTTGGTG | 960 |
| GAAGTAATTG | ATTTATTGAA | GTAGACTTAA | AAAAATGTTT | TGATACAATT | TCTCATGATT | 1020 |
| TAATTATTAA | AGAATTAAAA | AGATATATTT | CAGATAAAGG | TTTTATTGAT | TTAGTATATA | 1080 |
| AATTATTAAG | AGCTGGTTAT | ATTGATGAGA | AAGGAACTTA | TCATAAACCT | ATATTAGGTT | 1140 |
| TACCTCAAGG | ATCATTAATT | AGTCCTATCT | TATGTAATAT | TGTAATAACA | TTGGTAGATA | 1200 |
| ATTGATTAGA | AGATTATATT | AATTTATATA | ATAAAGGTAA | AGTTAAAAAA | CAACATCCTA | 1260 |
| CATATAAAAA | ATTATCAAGA | ATAATTGCAA | AAGCTAAAAT | ATTTTCGACA | AGATTAAAAT | 1320 |
| TACATAAAGA | AAGAGCTAAA | GGCCCACTAT | TTATTTATAA | TGATCCTAAT | TTCAAGAGAA | 1380 |

```
TAAAATACGT TAGATATGCA GATGATATTT TAATTGGGGT ATTAGGTTCA AAAAATGATT    1440

GTAAAATAAT CAAAGAGAT TTAAACAATT TTTTAAATTC ATTAGGTTTA ACTATAAATG    1500

AAGAAAAAAC TTTAATTACT TGTGCAACTG AACTACCAGC AAGATTTTTA GGTTATAATA    1560

TTTCAATTAC ACCTTTAAAA AGAATACCTA CAGTTACTAA ACTAATTAGA GGTAAACTTA    1620

TTAGAAGTAG AAATACAACT AGACCTATTA TTAATGCACC AATTAGAGAT ATTATCAATA    1680

AATTAGCTAC TAATGGATAT TGTAAGCATA ATAAAAATGG TAGAATAGGA GTGCCTACAA    1740

GAGTAGGTAG ATGACTATAT GAAGAACCTA GAACAATTAT TAATAATTAT AAAGCGTTAG    1800

GTAGAGGTAT CTTAAATTAT TATAAATTAG CTACTAATTA TAAAAGATTA AGAGAAAGAA    1860

TCTATTACGT ATTATATTAT TCATGTGTAT TAACTTTAGC TAGTAAATAT AGATTAAAAA    1920

CAATAAGTAA AACTATTAAA AAATTTGGTT ATAATTTAAA TATTATTGAA AATGATAAAT    1980

TAATTGCCAA TTTTCCAAGA AATACTTTTG ATAATATCAA AAAAATTGAA AATCATGGTA    2040

TATTTATATA TATATCAGAA GCTAAAGTAA CTGATCCTTT TGAATATATC GATTCAATTA    2100

AATATATATT ACCTACAGCT AAAGCTAATT TTAATAAACC TTGTAGTATT TGTAATTCAA    2160

CTATTGATGT AGAAATACAT CATGTTAAAC AATTACATAG AGGTATATTA AAAGCACTTA    2220

AAGATTATAT TCTAGGTAGA ATAATTACCA TAAACAGAAA ACAAATTCCA TTATGTAAAC    2280

AATGTCATAT TAAAACACAT AAAAATAAAT TTAAAATAT AGGACCTGGT ATATAAAATC    2340

TATTATTAAT GATACTCAAT ATGGAAAGCC GTATGATGGG AAACTATCAC GTACGGTTTG    2400

GGAAAGGCTC TTTAACACGT GGCAACATAG GTTAATTTGC TATTTCAT              2448
```

( 2 ) INFORMATION FOR SEQ ID NO:3:

( i ) SEQUENCE CHARACTERISTICS:
( A ) LENGTH: 777 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( x i ) SEQUENCE DESCRIPTION: SEQ ID NO:3:

```
Ala Pro Thr Ser Ala Tyr Ile Ser Leu Met Arg Thr Ala Leu Val Leu
1               5                   10                  15

Trp Ile Ile Asn Arg Tyr Leu Lys His Met Thr Asn Ser Val Gly Ala
            20                  25                  30

Asn Phe Thr Gly Thr Met Ala Cys His Lys Thr Pro Met Ile Ser Val
        35                  40                  45

Gly Gly Val Lys Cys Tyr Met Val Arg Leu Thr Asn Phe Leu Gln Val
    50                  55                  60

Phe Ile Arg Ile Thr Ile Ser Ser Tyr His Leu Asp Met Val Lys Gln
65                  70                  75                  80

Val Trp Leu Phe Tyr Val Glu Val Ile Arg Leu Trp Phe Ile Val Leu
                85                  90                  95

Asp Ser Thr Gly Ser Val Lys Lys Met Lys Asp Thr Asn Asn Thr Lys
            100                 105                 110

Gly Asn Thr Lys Ser Glu Gly Ser Thr Glu Arg Gly Asn Ser Trp Val
            115                 120                 125

Asp Arg Gly Met Val Val Pro Asn Thr Gln Met Lys Met Arg Phe Leu
        130                 135                 140

Asn Gln Val Arg Tyr Tyr Ser Val Asn Asn Asn Leu Lys Met Gly Lys
145                 150                 155                 160
```

-continued

```
Asp  Thr  Asn  Ile  Glu  Leu  Ser  Lys  Asp  Thr  Ser  Thr  Ser  Asp  Leu  Leu
               165                 170                      175

Glu  Phe  Glu  Lys  Leu  Val  Met  Asp  Asn  Met  Asn  Glu  Asn  Met  Asn
               180                 185                      190

Asn  Asn  Leu  Leu  Ser  Ile  Met  Lys  Asn  Val  Asp  Met  Leu  Met  Leu  Ala
               195                 200                      205

Tyr  Asn  Arg  Ile  Lys  Ser  Lys  Pro  Gly  Asn  Met  Thr  Pro  Gly  Thr  Thr
          210                 215                      220

Leu  Glu  Thr  Leu  Asp  Gly  Met  Asn  Met  Met  Tyr  Leu  Asn  Lys  Leu  Ser
225                      230                      235                      240

Asn  Glu  Leu  Gly  Thr  Gly  Lys  Phe  Lys  Phe  Lys  Pro  Met  Arg  Met  Val
                    245                 250                      255

Asn  Ile  Pro  Lys  Pro  Lys  Gly  Gly  Met  Arg  Pro  Leu  Ser  Val  Gly  Asn
                260                 265                      270

Pro  Arg  Asp  Lys  Ile  Val  Gln  Glu  Val  Met  Arg  Met  Ile  Leu  Asp  Thr
               275                 280                      285

Ile  Phe  Asp  Lys  Lys  Met  Ser  Thr  His  Ser  His  Gly  Phe  Arg  Lys  Asn
     290                      295                      300

Met  Ser  Cys  Gln  Thr  Ala  Ile  Trp  Glu  Val  Arg  Asn  Met  Phe  Gly  Gly
305                      310                      315                      320

Ser  Asn  Trp  Phe  Ile  Glu  Val  Asp  Leu  Lys  Lys  Cys  Phe  Asp  Thr  Ile
                    325                 330                      335

Ser  His  Asp  Leu  Ile  Ile  Lys  Glu  Leu  Lys  Arg  Tyr  Ile  Ser  Asp  Lys
               340                 345                      350

Gly  Phe  Ile  Asp  Leu  Val  Tyr  Lys  Leu  Leu  Arg  Ala  Gly  Tyr  Ile  Asp
          355                 360                      365

Glu  Lys  Gly  Thr  Tyr  His  Lys  Pro  Met  Leu  Gly  Leu  Pro  Gln  Gly  Ser
     370                      375                      380

Leu  Ile  Ser  Pro  Ile  Leu  Cys  Asn  Ile  Val  Met  Thr  Leu  Val  Asp  Asn
385                      390                      395                      400

Trp  Leu  Glu  Asp  Tyr  Ile  Asn  Leu  Tyr  Asn  Lys  Gly  Lys  Val  Lys  Lys
                    405                 410                      415

Gln  His  Pro  Thr  Tyr  Lys  Lys  Leu  Ser  Arg  Met  Ile  Ala  Lys  Ala  Lys
               420                 425                      430

Met  Phe  Ser  Thr  Arg  Leu  Lys  Leu  His  Lys  Glu  Arg  Ala  Lys  Gly  Pro
          435                 440                      445

Thr  Phe  Ile  Tyr  Asn  Asp  Pro  Asn  Phe  Lys  Arg  Met  Lys  Tyr  Val  Arg
          450                 455                      460

Tyr  Ala  Asp  Asp  Ile  Leu  Ile  Gly  Val  Leu  Gly  Ser  Lys  Asn  Asp  Cys
465                      470                      475                      480

Lys  Met  Ile  Lys  Arg  Asp  Leu  Asn  Asn  Phe  Leu  Asn  Ser  Leu  Gly  Leu
               485                 490                      495

Thr  Met  Asn  Glu  Glu  Lys  Thr  Leu  Ile  Thr  Cys  Ala  Thr  Glu  Thr  Pro
               500                 505                      510

Ala  Arg  Phe  Leu  Gly  Tyr  Asn  Ile  Ser  Ile  Thr  Pro  Leu  Lys  Arg  Met
          515                 520                      525

Pro  Thr  Val  Thr  Lys  Thr  Ile  Arg  Gly  Lys  Thr  Ile  Arg  Ser  Arg  Asn
     530                      535                      540

Thr  Thr  Arg  Pro  Ile  Ile  Asn  Ala  Pro  Ile  Arg  Asp  Ile  Ile  Asn  Lys
545                      550                      555                      560

Leu  Ala  Thr  Asn  Gly  Tyr  Cys  Lys  His  Asn  Lys  Asn  Gly  Arg  Met  Gly
                    565                 570                      575

Val  Pro  Thr  Arg  Val  Gly  Arg  Trp  Thr  Tyr  Glu  Glu  Pro  Arg  Thr  Ile
```

-continued

```
                       580                           585                           590
        Ile  Asn  Asn  Tyr  Lys  Ala  Leu  Gly  Arg  Gly  Ile  Leu  Asn  Tyr  Tyr  Lys
                  595                           600                           605

Leu  Ala  Thr  Asn  Tyr  Lys  Arg  Leu  Arg  Glu  Arg  Ile  Tyr  Tyr  Val  Leu
                  610                           615                           620

Tyr  Tyr  Ser  Cys  Val  Leu  Thr  Leu  Ala  Ser  Lys  Tyr  Arg  Leu  Lys  Thr
        625                      630                      635                      640

Met  Ser  Lys  Thr  Ile  Lys  Lys  Phe  Gly  Tyr  Asn  Leu  Asn  Ile  Ile  Glu
                            645                      650                      655

Asn  Asp  Lys  Leu  Ile  Ala  Asn  Phe  Pro  Arg  Asn  Thr  Phe  Asp  Asn  Ile
                       660                      665                      670

Lys  Lys  Ile  Glu  Asn  His  Gly  Met  Phe  Met  Tyr  Met  Ser  Glu  Ala  Lys
                  675                      680                      685

Val  Thr  Asp  Pro  Phe  Glu  Tyr  Ile  Asp  Ser  Ile  Lys  Tyr  Met  Leu  Pro
             690                      695                      700

Thr  Ala  Lys  Ala  Asn  Phe  Asn  Lys  Pro  Cys  Ser  Ile  Cys  Asn  Ser  Thr
        705                      710                      715                      720

Ile  Asp  Val  Glu  Met  His  His  Val  Lys  Gln  Leu  His  Arg  Gly  Met  Leu
                            725                      730                      735

Lys  Ala  Thr  Lys  Asp  Tyr  Ile  Thr  Gly  Arg  Met  Ile  Thr  Met  Asn  Arg
                       740                      745                      750

Lys  Gln  Ile  Pro  Leu  Cys  Lys  Gln  Cys  His  Ile  Lys  Thr  His  Lys  Asn
                  755                      760                      765

Lys  Phe  Lys  Asn  Met  Gly  Pro  Gly  Met
                                 775
```

(2) INFORMATION FOR SEQ ID NO:4:

(i) SEQUENCE CHARACTERISTICS:
        (A) LENGTH: 785 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:4:

```
        Ala  Pro  Phe  Arg  Leu  Ile  Tyr  His  Cys  Ile  Glu  Val  Leu  Ile  Asp  Lys
        1                   5                        10                       15

His  Ile  Ser  Val  Tyr  Ser  Ile  Asn  Glu  Asn  Phe  Thr  Val  Ser  Phe  Trp
                       20                       25                       30

Phe  Trp  Leu  Leu  Val  Val  Thr  Tyr  Met  Val  Phe  Arg  Tyr  Val  Asn  His
                  35                       40                       45

Met  Ala  Tyr  Pro  Val  Gly  Ala  Asn  Ser  Thr  Gly  Thr  Met  Ala  Cys  His
             50                       55                       60

Lys  Ser  Ala  Gly  Val  Lys  Gln  Pro  Ala  Gln  Gly  Lys  Asn  Cys  Pro  Met
        65                       70                       75                       80

Ala  Arg  Leu  Thr  Asn  Ser  Cys  Lys  Glu  Cys  Leu  Gly  Phe  Ser  Leu  Thr
                            85                       90                       95

Pro  Ser  His  Leu  Gly  Ile  Val  Ile  His  Ala  Tyr  Val  Leu  Glu  Glu  Glu
                       100                      105                      110

Val  His  Glu  Leu  Thr  Lys  Asn  Glu  Ser  Leu  Ala  Leu  Ser  Lys  Ser  Trp
                  115                      120                      125

His  Leu  Glu  Gly  Cys  Thr  Ser  Ser  Asn  Gly  Lys  Leu  Arg  Asn  Thr  Gly
             130                      135                      140
```

```
Leu  Ser  Glu  Arg  Gly  Asn  Pro  Gly  Asp  Asn  Gly  Val  Phe  Met  Val  Pro
145                 150                 155                      160

Lys  Phe  Asn  Leu  Asn  Lys  Ala  Arg  Tyr  Phe  Ser  Thr  Leu  Ser  Lys  Leu
                    165                 170                      175

Asn  Ala  Arg  Lys  Glu  Asp  Ser  Leu  Ala  Tyr  Leu  Thr  Lys  Ile  Asn  Thr
               180                 185                      190

Thr  Asp  Phe  Ser  Glu  Leu  Asn  Lys  Leu  Met  Glu  Asn  Asn  His  Asn  Lys
          195                 200                      205

Thr  Glu  Thr  Ile  Asn  Thr  Arg  Ile  Leu  Lys  Leu  Met  Ser  Asp  Ile  Arg
     210                 215                      220

Met  Leu  Leu  Ile  Ala  Tyr  Asn  Lys  Ile  Lys  Ser  Lys  Lys  Gly  Asn  Met
225                 230                 235                           240

Ser  Lys  Gly  Ser  Asn  Asn  Ile  Thr  Leu  Asp  Gly  Ile  Asn  Ile  Ser  Tyr
                    245                 250                      255

Leu  Asn  Lys  Leu  Ser  Lys  Asp  Ile  Asn  Thr  Asn  Met  Phe  Lys  Phe  Ser
                    260                 265                      270

Pro  Val  Arg  Arg  Val  Glu  Ile  Pro  Lys  Thr  Ser  Gly  Gly  Phe  Arg  Pro
               275                 280                 285

Leu  Ser  Val  Gly  Asn  Pro  Arg  Glu  Lys  Ile  Val  Gln  Glu  Ser  Met  Arg
     290                 295                      300

Met  Met  Leu  Glu  Ile  Ile  Tyr  Asn  Asn  Ser  Phe  Ser  Tyr  Tyr  Ser  His
305                 310                      315                      320

Gly  Phe  Arg  Pro  Asn  Leu  Ser  Cys  Leu  Thr  Ala  Ile  Ile  Gln  Cys  Lys
                    325                 330                      335

Asn  Tyr  Met  Gln  Tyr  Cys  Asn  Trp  Phe  Ile  Lys  Val  Asp  Leu  Asn  Lys
               340                 345                      350

Cys  Phe  Asp  Thr  Ile  Pro  His  Asn  Met  Leu  Ile  Asn  Val  Leu  Asn  Glu
          355                 360                      365

Arg  Ile  Lys  Asp  Lys  Gly  Phe  Met  Asp  Leu  Leu  Tyr  Lys  Leu  Leu  Arg
     370                 375                      380

Ala  Gly  Tyr  Val  Asp  Lys  Asn  Asn  Tyr  His  Asn  Thr  Thr  Leu  Gly
385                 390                 395                           400

Ile  Pro  Gln  Gly  Ser  Val  Val  Ser  Pro  Ile  Leu  Cys  Asn  Ile  Phe  Leu
               405                 410                      415

Asp  Lys  Leu  Asp  Lys  Tyr  Leu  Glu  Asn  Lys  Phe  Glu  Asn  Glu  Phe  Asn
               420                 425                      430

Thr  Gly  Asn  Met  Ser  Asn  Arg  Gly  Arg  Asn  Pro  Ile  Tyr  Asn  Ser  Leu
          435                 440                      445

Ser  Ser  Lys  Ile  Tyr  Arg  Cys  Lys  Leu  Leu  Ser  Glu  Lys  Leu  Lys  Leu
     450                 455                      460

Ile  Arg  Leu  Arg  Asp  His  Tyr  Gln  Arg  Asn  Met  Gly  Ser  Asp  Lys  Ser
465                 470                      475                      480

Phe  Lys  Arg  Ala  Tyr  Phe  Val  Arg  Tyr  Ala  Asp  Asp  Ile  Ile  Ile  Gly
                    485                 490                      495

Val  Met  Gly  Ser  His  Asn  Asp  Cys  Lys  Asn  Ile  Leu  Asn  Asp  Ile  Asn
               500                 505                      510

Asn  Phe  Leu  Lys  Glu  Asn  Leu  Ser  Ile  Val  Met  Lys  Leu  Asn  Lys  His
          515                 520                      525

Gly  Tyr  Cys  Ser  His  Gly  Ile  Leu  Gly  Lys  Pro  Gly  Met  Ser  Ile  Asn
          530                 535                      540

Met  Asp  Lys  Ser  Val  Ile  Lys  His  Ser  Lys  Glu  Gly  Val  Ser  Phe  Leu
545                 550                      555                      560

Gly  Tyr  Asp  Val  Lys  Val  Thr  Pro  Trp  Glu  Lys  Arg  Pro  Tyr  Arg  Met
               565                 570                      575
```

|     |     |     |     |     |     |     |     |     |     |     |     |     |     |     |
| --- | --- | --- | --- | --- | --- | --- | --- | --- | --- | --- | --- | --- | --- | --- |
| Ile | Lys | Lys | Gly | Asp | Asn | Phe | Ile | Arg | Val | Arg | His | His | Thr | Ser | Leu |
|     |     |     | 580 |     |     |     |     | 585 |     |     |     |     | 590 |     |     |
| Val | Val | Asn | Ala | Pro | Ile | Arg | Arg | Gly | Val | Gly | Arg | Leu | Ile | His | Glu |
|     |     | 595 |     |     |     |     | 600 |     |     |     |     | 605 |     |     |     |
| Glu | Met | Lys | Thr | Ile | Leu | Met | His | Tyr | Leu | Ala | Val | Gly | Arg | Gly | Ile |
|     | 610 |     |     |     |     | 615 |     |     |     |     | 620 |     |     |     |     |
| Met | Asn | Tyr | Tyr | Arg | Leu | Ala | Thr | Asn | Phe | Thr | Thr | Leu | Arg | Gly | Arg |
| 625 |     |     |     |     | 630 |     |     |     |     | 635 |     |     |     |     | 640 |
| Ile | Thr | Tyr | Ile | Leu | Phe | Tyr | Ser | Cys | Cys | Leu | Thr | Leu | Ala | Arg | Lys |
|     |     |     |     | 645 |     |     |     |     | 650 |     |     |     |     | 655 |     |
| Phe | Lys | Leu | Asn | Thr | Val | Lys | Lys | Val | Ile | Leu | Lys | Phe | Gly | Lys | Val |
|     |     |     | 660 |     |     |     |     | 665 |     |     |     |     | 670 |     |     |
| Leu | Val | Asp | Pro | His | Ser | Lys | Val | Ser | Phe | Ser | Ile | Asp | Asp | Phe | Lys |
|     |     |     | 675 |     |     |     | 680 |     |     |     |     | 685 |     |     |     |
| Ile | Arg | His | Lys | Met | Asn | Met | Thr | Asp | Ser | Asn | Tyr | Thr | Pro | Asp | Glu |
|     |     | 690 |     |     |     |     | 695 |     |     |     |     | 700 |     |     |     |
| Ile | Leu | Asp | Arg | Tyr | Lys | Tyr | Met | Leu | Pro | Arg | Ser | Leu | Ser | Leu | Phe |
| 705 |     |     |     |     | 710 |     |     |     |     | 715 |     |     |     |     | 720 |
| Ser | Gly | Ile | Cys | Gln | Ile | Cys | Gly | Ser | Lys | His | Asp | Leu | Glu | Val | His |
|     |     |     |     | 725 |     |     |     |     | 730 |     |     |     |     | 735 |     |
| His | Val | Arg | Thr | Leu | Asn | Asn | Ala | Ala | Asn | Lys | Ile | Lys | Asp | Asp | Tyr |
|     |     |     | 740 |     |     |     |     | 745 |     |     |     |     | 750 |     |     |
| Leu | Leu | Gly | Arg | Met | Ile | Lys | Met | Asn | Arg | Lys | Gln | Ile | Thr | Ile | Cys |
|     |     | 755 |     |     |     |     | 760 |     |     |     |     | 765 |     |     |     |
| Lys | Thr | Cys | His | Phe | Lys | Val | His | Gln | Gly | Lys | Tyr | Asn | Gly | Pro | Gly |
|     | 770 |     |     |     |     | 775 |     |     |     |     | 780 |     |     |     |     |
| Leu |
| 785 |

( 2 ) INFORMATION FOR SEQ ID NO:5:

( i ) SEQUENCE CHARACTERISTICS:
        ( A ) LENGTH: 71 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:5:

```
TTTTAGTAGC  TGGTCATGCT  GTATTAATAA  TTTTCTTCTT  AGTAATGCCT  GCTTTAATAG        60

GAGGTTTTGG  T                                                                 71
```

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:6:

```
TCGAGGTCGA  CGGTATC                                                           17
```

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:7:

CGCTCTAGAA CTAGTGGATC     20

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:8:

TAATCATTAG ATTAGAATTA GCTGCACCTG     30

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:9:

AGAAAATCAT TAATACAGC     19

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:10:

CTAATACGAC TCACTATAGG GC     22

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:11:

CAAAAGCTGG GTACCGGGCC CCCCC 25

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:12:

TTTTAGTAGC TGGTCAGCTG TATT 24

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:13:

ACCAAAACCT CCTATTAAAG CAGGC 25

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:14:

GAGTTAAGCG GACCTGGGGT GCAG 24

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:15:

ATTAAGTCTT GGGAATGCCA TGTC 24

( 2 ) INFORMATION FOR SEQ ID NO:16:

( i ) SEQUENCE CHARACTERISTICS:
        ( A ) LENGTH: 180 base pairs
        ( B ) TYPE: nucleic acid
        ( C ) STRANDEDNESS: double
        ( D ) TOPOLOGY: linear (i i) MOLECULE TYPE: cDNA (i i i) HYPOTHETICAL: NO (x i) SEQUENCE DESCRIPTION: SEQ ID NO:16:

| GAGTTAAGCG | GACCTGGGGT | GCAGTACATT | GCAGATAATC | AATTATACAA | TGCTATAATA | 60 |
| ACTGCACATG | CGATCTTAAT | GATTTTCTTT | ATGGTTATGC | CAGCATTAAT | AGGTGGATTT | 120 |
| GGTAATTTCT | TGTTACCATT | ATTAGTAGGG | GGTCCTGACA | TGGCATTCCC | AAGACTTAAT | 180 |

(2) INFORMATION FOR SEQ ID NO:17:

(i) SEQUENCE CHARACTERISTICS:
(A) LENGTH: 105 base pairs
(B) TYPE: nucleic acid
(C) STRANDEDNESS: double
(D) TOPOLOGY: linear (i i) MOLECULE TYPE: cDNA (i i i) HYPOTHETICAL: NO (x i) SEQUENCE DESCRIPTION: SEQ ID NO:17:

| TAATCATTAG | ATTAGAATTA | GCTGCACCTG | GTTCACAATA | TTTACATGGT | AATTCACAGT | 60 |
| TATTTAATGT | TTTAGTAGTT | GGTCATGCTG | TATTAATGAT | TTTCT | | 105 |